(12) United States Patent
Rybkin

(10) Patent No.: US 9,058,635 B1
(45) Date of Patent: Jun. 16, 2015

(54) MEDICAL PATIENT DATA COLLABORATION SYSTEM

(71) Applicant: Alexander Valentine Rybkin, Belmont, CA (US)

(72) Inventor: Alexander Valentine Rybkin, Belmont, CA (US)

(*) Notice: Subject to any disclaimer, the term of this patent is extended or adjusted under 35 U.S.C. 154(b) by 204 days.

(21) Appl. No.: 13/631,079

(22) Filed: Sep. 28, 2012

Related U.S. Application Data

(60) Provisional application No. 61/541,008, filed on Sep. 29, 2011.

(51) Int. Cl.
 G06Q 50/00 (2012.01)
 G06Q 50/22 (2012.01)
 G06Q 50/24 (2012.01)

(52) U.S. Cl.
 CPC ............. *G06Q 50/22* (2013.01); *G06Q 50/24* (2013.01)

(58) Field of Classification Search
 None
 See application file for complete search history.

(56) References Cited

U.S. PATENT DOCUMENTS

| 7,916,014 | B2 | 3/2011 | Rapaport et al. |
| 7,987,110 | B2 | 7/2011 | Cases et al. |
| 2004/0128163 | A1 | 7/2004 | Goodman et al. |
| 2010/0305972 | A1* | 12/2010 | McLaren et al. ................. 705/3 |
| 2010/0332509 | A1* | 12/2010 | Rogers et al. ................. 707/759 |
| 2011/0010200 | A1 | 1/2011 | Firozvi et al. |
| 2011/0153352 | A1 | 6/2011 | Semian |

* cited by examiner

*Primary Examiner* — Michelle L Le
(74) *Attorney, Agent, or Firm* — Knobbe Martens Olson & Bear LLP

(57) ABSTRACT

Systems and methods for mitigating breakdowns in communications among healthcare providers are described, among other features. A communications system can be provided for communicating patient information among health care providers, who may include clinicians, doctors, interns, residents, physician's assistants, nurses, or any other health care personnel. The communications system can enable tracking of the responsibility relationships between changing providers and patients. In addition, the communications system can allow rapid and reliable messaging between any provider and the provider responsible for the patient at any one time.

25 Claims, 29 Drawing Sheets

FIG. 8

| | | | | | |
|---|---|---|---|---|---|
| | ○○○ | | | | |
| | ▲▼ | + | ⊙ http://10.211.55.4/Pagerdoc/Account/Users | ⟲ | Q▾ Google |

Caredination

CAREDINATION

Welcome manager Log Off

| Home | Users | Log | ACGME |

Search by User name: [        ] (Search)

Users: 10

| User Name | | Email | Status | Roles | Creation Date |
|---|---|---|---|---|---|
| Edit | 000000 | ucsf@ucsf.edu | offline | Default | 5/8/2011 4:57:39 PM |
| Edit | 000018 | ucsf@ucsf.edu | offline | Doctor | 5/4/2011 10:06:02 PM |
| Edit | 000034 | ucsf@ucsf.edu | offline | Doctor | 5/8/2011 2:35:12 PM |
| Edit | 000059 | ucsf@ucsf.edu | offline | Doctor | 5/8/2011 1:30:53 PM |
| Edit | 000067 | ucsf@ucsf.edu | offline | Doctor | 5/8/2011 3:18:42 PM |
| Edit | 000075 | ucsf@ucsf.edu | offline | Doctor | 5/8/2011 4:59:18 PM |
| Edit | 019091 | dummy_email@ucsf.edu | offline | Doctor | 5/18/2011 11:14:48 PM |
| Edit | 031989 | 031989@yahoo.com | offline | Doctor | 2/17/2011 2:47:47 PM |
| Edit | 111203 | ucsf@ucsf.edu | offline | Doctor | 5/8/2011 7:00:36 PM |
| Edit | manager | foo@sfdph.org | offline | Manager | 2/20/2011 4:41:55 PM |

<< Page: 1 >>

FIG. 10

CAREDINATION

Welcome manager | Log Off

[Home] [Users] [Log] [ACGME]

Log Entries

Search:

Patient MRN: [____] Timeframe: [1 week ▼] (Search)

| ID | Action | Description | UserName | Patient_ID | Timestamp |
|----|--------|-------------|----------|------------|-----------|
| 895 | Logon | | manager | | 6/2/2011 2:13 PM |
| 894 | Logoff | | | 031989 | 6/2/2011 2:12 PM |

FIG. 11

CAREDINATION http://10.211.55.4/Pagerdoc/Provider

Caredination

Welcome manager Log Off

| Home | Users | Log | ACGME |

Work Hours by Doctor

| chn | Last Name | First Name | Duty Hrs This Week | Duty Hrs (4 week avg) | On Times (hrs) | Off Times (hrs) | Status |
|---|---|---|---|---|---|---|---|
| 000018 | PHYSICIAN | STAFF | 0.00 | 0.00 | None | None | Off |
| 000059 | ... | ... | 0.00 | 0.31 | 1.3 | None | Off |
| 031989 | ... | ... | 78.06 | 152.05 | 27.2, 0.0, 282.0, 0.5, 0.0, 220.4, 76.4, 0.1, 0.0 0.0, 0.0, 1.5 | 0.0, 3.8, 0.0, 0.0, 0.0, 0.0, 0.0, 0.0, 15.3, 0.0 0.0, 0.0 | Inhouse |
| 019091 | ... | ... | 0.00 | 0.00 | 0.0 | none | Off |

Create New

FIG. 12

CAREDINATION

Filter by Service [Go]

My Teams

| | name | description | service | location | Base | Role | |
|---|---|---|---|---|---|---|---|
| Edit | Medicine 1A | Just plain old medicine inpatient team | Family Medicine | 5A | Inpatient | Primary | Remove me from team |
| Edit | Medicine 1B | Another medicine team edit | Family Medicine | 4A | Inpatient | Primary | Remove me from team |

Other Teams

| | name | description | service | location | Base | Role | |
|---|---|---|---|---|---|---|---|
| Edit | Ortho Consult | Orthopedic Surgery consult service | Ortho Consult | none | Inpatient | Consulting | Add me to team |
| Edit | Medicine 1C | another sample medicine team | Internal Medicine | | Inpatient | Primary | Add me to team |
| Edit | L & D Team A | Ob Gyn team | Labor and Delivery | 6G | Inpatient | Primary | Add me to team |
| Edit | Gyn A | | Gynecology | | Outpatient | Primary | Add me to team |
| Edit | IR Consult | | Radilogy IR | | Inpatient | Consulting | Add me to team |
| Edit | Neurology Consult | | Neurology | | Inpatient | Consulting | Add me to team |

Create New Team | Edit Services

FIG. 15

CAREDINATION

Welcome 031989 | Log Off

| Home | Tasks | Patients | Teams | My Profile | Manage |

Page 1 of 1    Quick Navigation

Team IR Consult | Service: Radiology IR | Base: Inpatient

| ID | Description | Service Info | Issues | Key Meds | Tasks | Daily Log |
|---|---|---|---|---|---|---|
| Sample Patient 01586765 IR Consult Loc: Adm: 3/24/2012 (HD: 173) PMD: Contact: | 25 yo male BIBA after MVC. On exam seat belt sign, abdominal pain, vomiting  Allergies: | • Radiology IR Info: 7/22/2012  This is IR specific information  [+] | • Normal  Anticipated:  • foo  [+] | • Aspirin  [+] | • ☐ ir task  [+] | No items  [+] |
| ID | Description | Service Info | Issues | Key Meds | Tasks | Daily Log |

Page 1 of 1 home

CAREDINATION

| iSample, Patient 4B | Doe, Jane 5A | Doe, John 7dog |
|---|---|---|
| 25 yo male BIBA after MVC ... | 25 yo female with RUQ pai ... | 37 yo male, with h/o ETOH ... |
| • ☐ sample task<br>• ☐ ir task<br>• ☐ third task<br>• ☐ fourth task | • ☐ Contact PMD<br>• ☐ F/u EKG | • ☐ Consult Cards<br>• ☐ F/u Bcx<br>• ☐ Consult Neuro<br>• ☐ F/u EKG |
| [ completed ] [+] | [ completed ] [+] | [ completed ] [+] |

[ Print ] | [ Grid ]

FIG. 22

MEDICAL PATIENT DATA COLLABORATION SYSTEM

RELATED APPLICATION

This application claims priority under 35 U.S.C. §119(e) to U.S. Provisional Application No. 61/541,008, filed Sep. 29, 2011, titled "Medical Patient Data Collaboration System," the disclosure of which is hereby incorporated by reference in its entirety.

BACKGROUND

Multiple clinicians may see a patient during the course of a patient's hospitalization, as clinicians change shifts and work assignments. In many inpatient units there are white-boards that list the patient and the respective nurses, doctors, and technologists who are assigned to them. These boards usually list contact information for the personnel, such as pagers and telephone numbers. If someone needs to reach the healthcare provider regarding the patient, the board is consulted so that the appropriate provider can be paged.

SUMMARY

The constant turnover of personnel makes it difficult to determine who holds any particular role in the care of the patient at any one time. Described herein are systems and methods for communication among healthcare providers, which can permit tracking of the responsibility relationships among changing providers and patients, and can therefore allow rapid and reliable messaging between any provider and the provider responsible for the patient at any one time. The system and method described herein can also facilitate a dialogue among the changing providers about the care of the patient.

In several embodiments, a method of making patient care messages available to healthcare providers on different shifts includes electronically generating a provider assignment user interface for presentation to a user. The provider assignment user interface can include functionality for the user to assign a patient to a first team of healthcare providers. The method can also include, in response to the patient being assigned to the first team of healthcare providers: providing the first team of healthcare providers with access to a patient messaging user interface, where the patient messaging user interface can enable the first team of healthcare providers to electronically post messages regarding care of the patient for access by each member of the first team of healthcare providers and for access by a second team of healthcare providers subsequently assigned to the patient, without requiring the members of the first team of healthcare providers to know an identity of any of the second team of healthcare providers when electronically posting the messages, where the messages include a task having a deadline; providing a patient handoff user interface that provides functionality for care of the patient to be handed off from the first team of healthcare providers to the second team of healthcare providers; providing the second team of healthcare providers with access to the posted messages regarding the patient posted by the first team of healthcare providers in response to a handoff of the patient care occurring via the patient handoff user interface, wherein said providing the second team with access to the posted messages comprises sending a notification regarding the task to a member of the second team of healthcare providers that is a student provider before sending the notification to a supervisory provider of the second team of healthcare providers; and in response to determining that the student provider failed to respond to the message, escalating the notification of the task to the supervisory provider. The method may be implemented by a computer system including computer hardware.

In various embodiments, a system for making patient care messages available to healthcare providers on different shifts can include a patient handoff component that can provide a patient handoff user interface that provides functionality for care of a patient to be handed off from a first team of healthcare providers initially assigned to care for the patient to a second team of healthcare providers subsequently assigned to care for the patient. The system can also include a messaging component that includes computer hardware. The messaging component can provide the first team of healthcare providers with access to a patient messaging user interface while the first team of healthcare providers is assigned to care for the patient. The patient messaging user interface can enable members of the first team of healthcare providers to post messages regarding care of the patient for access by each other and by the second team of healthcare providers, without the first healthcare provider having to know an identity of the second healthcare provider. In response to care of the patient being transferred from the first team of healthcare providers to the second team of healthcare providers, the messaging component can also automatically provide the second team of healthcare providers with access to the posted messages regarding the patient posted by the first team of healthcare providers.

In several embodiments, non-transitory physical computer storage can include instructions stored thereon that, when executed by one or more processors, cause the one or more processors to implement a system for making patient care messages available to healthcare providers on different shifts. The system can include: a messaging component that can: electronically generate a patient messaging user interface; provide a first team of healthcare providers with access to the patient messaging user interface while the first team of healthcare providers is assigned to care for the patient, where the patient messaging user interface can enable the first team of healthcare providers to post messages regarding care of the patient for access by each member of the first team of healthcare providers and by the second team of healthcare providers, without the first team of healthcare providers having to know an identity of the second team of healthcare providers when posting the messages; and automatically provide the second team of healthcare providers with access to the posted message regarding the patient posted by the first team of healthcare providers in response to care of the patient being transferred from the first team of healthcare providers to the second team of healthcare providers.

The systems and methods described herein can be implemented by a computer system comprising computer hardware. The computer system may include one or more physical computing devices, which may be geographically dispersed or co-located.

Certain aspects, advantages and novel features of the inventions are described herein. It is to be understood that not necessarily all such advantages may be achieved in accordance with any particular embodiment of the inventions disclosed herein. Thus, the inventions disclosed herein may be embodied or carried out in a manner that achieves or selects one advantage or group of advantages as taught herein without necessarily achieving other advantages as may be taught or suggested herein.

BRIEF DESCRIPTION OF THE DRAWINGS

The features disclosed herein are described below with reference to the drawings. Throughout the drawings, reference numbers are re-used to indicate correspondence between referenced elements. The drawings are provided to illustrate embodiments of the inventions described herein and not to limit the scope thereof.

FIGS. 4A through 22 illustrate embodiments of user interfaces that can be generated by the aggregator system.

DETAILED DESCRIPTION

I. Introduction

Figure 1:
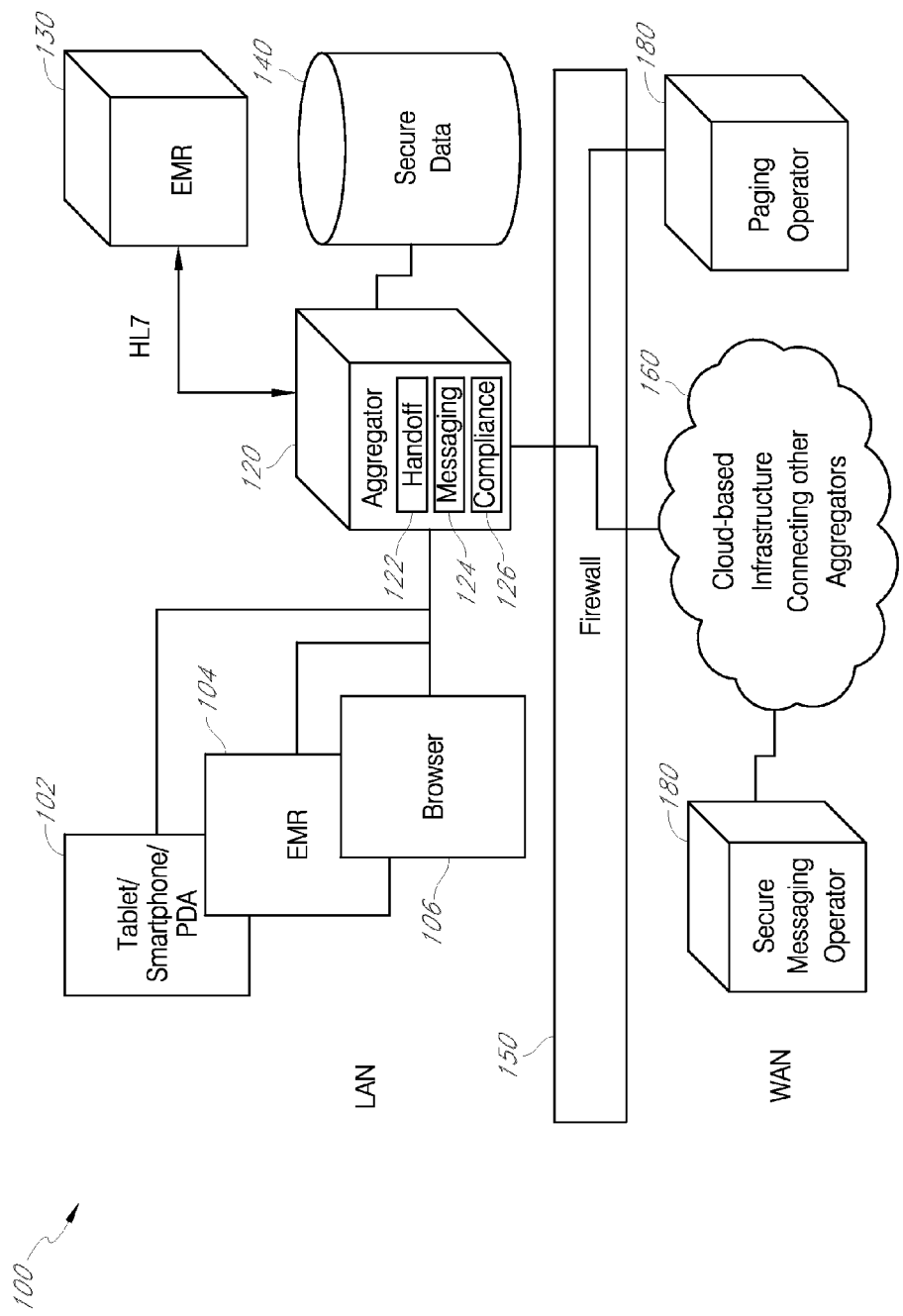
FIG. 1 illustrates an embodiment of a computing environment for providing access to an aggregator system.

Maintaining clinician schedules using white boards is a difficult and error-prone task. The clerk, who is in charge of updating the board, has to consult work schedules for doctors, nurses and other healthcare workers, keeping track of changes in real time. The reality is that work schedules contain errors, are out of date, or are simply unavailable to the clerks. As a result, the boards are frequently inaccurate. The physical boards are also inaccessible to the providers who practice elsewhere in the hospital or off-site. As a result, many providers do not know the other providers taking care of their patients. In a recent study of doctor-nurse communication, for example, nurses correctly identified their patients' doctors only 71% of the time. Doctors correctly identified their patients' nurses in only 36% of the time. O'Leary, K. J., J. A. Thompson, et al. (2010). "Patterns of nurse-physician communication and agreement on the plan of care." *Qual Saf Health Care* 19(3): 195-199, which is hereby incorporated by reference in its entirety. These misidentifications result in communication failures. Such "communication failures are a frequent cause of adverse events; the Joint Commission reports that such failures contributed to 65% of reported sentinel events." Sehgal, N. L. et al. (2010). "Patient Whiteboards as a Communication Tool in the Hospital Setting: A Survey of Practices and Recommendations." *Journal of Hospital Medicine* 5(4): 234-239, 234, which is hereby incorporated by reference in its entirety.

This confusion is not limited to doctors and nurses. For example, a pharmacist, upon detecting an error in the patient's medication, may need to contact the doctor who is in charge of the patient. The physician who is currently taking care of the patient may not be the person who ordered medication in the first place, because of the shift change and resulting handoff from one doctor to another. The pharmacist often then needs to contact the patient's unit, so that the unit clerk can consult the board and tell the pharmacist which doctor is currently in charge (and appropriate contact information). In the absence of the direct method to find the doctor in charge, the pharmacist wastes time trying to communicate time-sensitive and potentially life-saving information. Breakdown in communication is inevitable, however, if the information that the pharmacist gets from the board is inaccurate. In such cases the pharmacist is forced to make several calls to different clerks, who try to match up work schedules to obtain more accurate data. Even though the pharmacist detected the medication error, subsequent communication breakdown may result in an adverse outcome for the patient.

This disclosure described systems and methods for mitigating such breakdowns in communications, among other features. In several embodiments, a communications system is provided for communicating patient information among health care providers, who may include clinicians, doctors, interns, residents, physician's assistants, nurses, or any other health care personnel. The communications system can enable tracking of the responsibility relationships between changing providers and patients. In addition, the communications system can allow rapid and reliable messaging between any provider and the provider responsible for the patient at any one time. Further, the system can support asynchronous exchange of messages, which can take the form of interactive dialogue or conversation among two or more providers. It should be noted, however, that the claimed subject matter is not limited to implementations that solve any or all disadvantages noted in any part of this disclosure.

II. Example Communications System and Processes

With reference to FIG. 1, a computing environment 100 is shown for providing users with access to an aggregator system 120 (often referred to herein as an "aggregator 120"). The aggregator 120 includes hardware and/or software for performing handoff, messaging, and/or compliance functions. By way of example, the depicted embodiment of the aggregator 120 includes a handoff component 122, a messaging component 126, and a compliance component 126. Each of these components can be implemented in hardware and/or software.

Users of the aggregator 120 can include any provider or clinician, any hospital or clinical facility staff member (including clerical staff), and the like. In one embodiment, providers or other users connect to the aggregator 120 through a LAN, WAN, or other network (including optionally the Internet or wireless networks), using any client device. Some examples of client devices include computers or mobile devices 102, such as smart phones, laptops, touch pads, kiosks, desktops, and the like. Users can also access the aggregator 120 through an EMR application 104 and optionally using browser software 106 or other client software installed on a client device.

The aggregator 120 can include software that executes on one or more computing devices, such as one or more physical server computers. In embodiments where the aggregator 120 is implemented on multiple servers, these servers can be co-located or can be geographically separate (such as in separate data centers). In addition, the aggregator 120 can be implemented in a cloud computing platform, such as may be available from Amazon Web Services™, the Windows Azure™ Platform, or the like. For instance, the aggregator 120 can be implemented in one or more virtual machines that execute on one or more physical servers. Further, the aggregator 120 can include a server or appliance on the local area network, which is protected from the wide area network (e.g., the public Internet or other network) by a firewall or other security mechanism.

In several embodiments, the handoff component 122 of the aggregator 120 can allow providers to sign out or handoff patient care to one another at shift changes (or at other times). This handoff process can symbolically represent the transfer of responsibility for the care of a patient. The messaging component 126 can provide functionality for providers to send messages to one another and to subsequent providers on different shifts, without having to know the identity of these providers beforehand. The compliance component 126 can provide functionality for a clinical facility to comply with regulations related to patient care, such as regulations regarding working hours of medical trainees like interns and residents. It should be understood that any handoff functionality described herein can be implemented by the handoff component 122, any messaging functionality described herein can be implemented by the messaging component 124, and any compliance functionality described herein can be implemented by the compliance component 126. Any subset of the features described herein with respect to the aggregator 120 may be implemented in any given embodiment.

In several embodiments, the computing environment 100 can be implemented in a teaching hospital or other teaching clinical facility (including educational facilities for doctors, nurses, or other clinicians). The handoff, messaging, and compliance functionality (or any subset thereof) can facilitate more efficient and effective training for interns, residents, and other medical trainees, as will be described in greater detail herein. In addition, other aspects of the computing environment 100 shown in FIG. 1 are described in more detail below. However, the computing environment 100 need not be implemented in a teaching facility, but can be implemented in any facility.

Figure 2A:
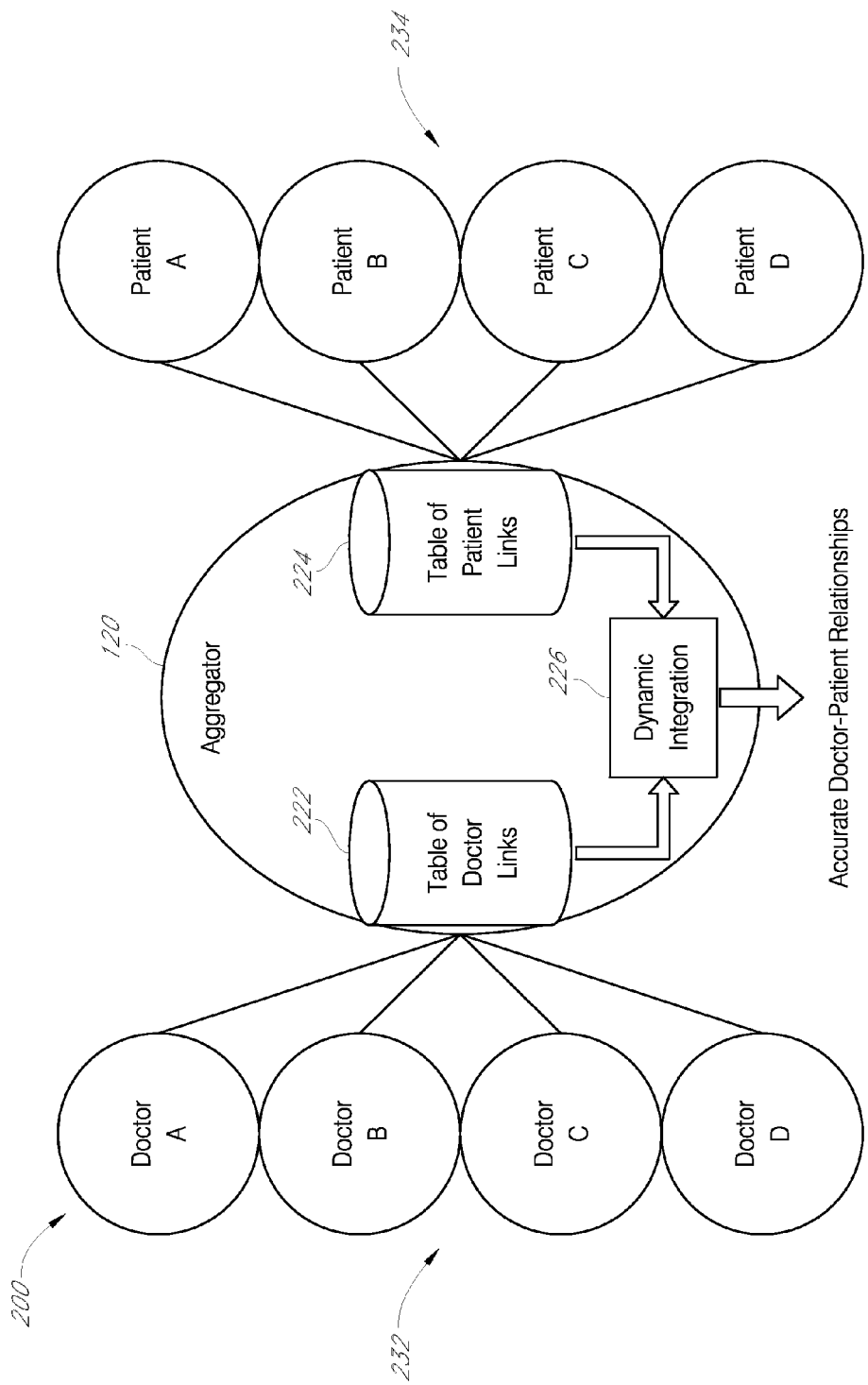
FIGS. 2A through 2D illustrate an embodiment of the aggregator system of FIG. 1 in the context of a patient handoff scenario.

Referring to FIG. 2A, to facilitate the handoff and messaging functionality, the aggregator 120 can monitor symbolic links between the providers and the patients and store these links in a database. As the totality of symbolic links may be constantly changing in real time (or near real time) in response to input by a plurality of providers 232 upon a plurality of patients 234, this is not a function that can be adequately performed by a human being as a mental process. When a provider 232 wishes to send a message about a patient 234, the aggregator 120 can consult a database having a table of doctor links 222 and a table of patient links 224. The aggregator 120 can access these tables to retrieving the symbolic links between the patient and the current responsible providers. The aggregator 120 can dynamically aggregate this information using an integration component 226 to construct a list of the providers 232 who are currently responsible for a given patient 234.

The aggregator 120 also has the capability in several embodiments to route messages to the responsible provider 232. Therefore, the aggregator 120 can allow sending of messages without prospective knowledge of the recipient. The messages are routed automatically to the provider 232 in charge at any one time. In one embodiment, these messages may include notifications and reminders (of tasks to be performed, laboratory studies to be checked, etc.), which are scheduled without advance knowledge of the recipient. The aggregator 120 determines the correct recipient at the scheduled time (see, e.g., below with respect to FIG. 3B).

Figure 2B:
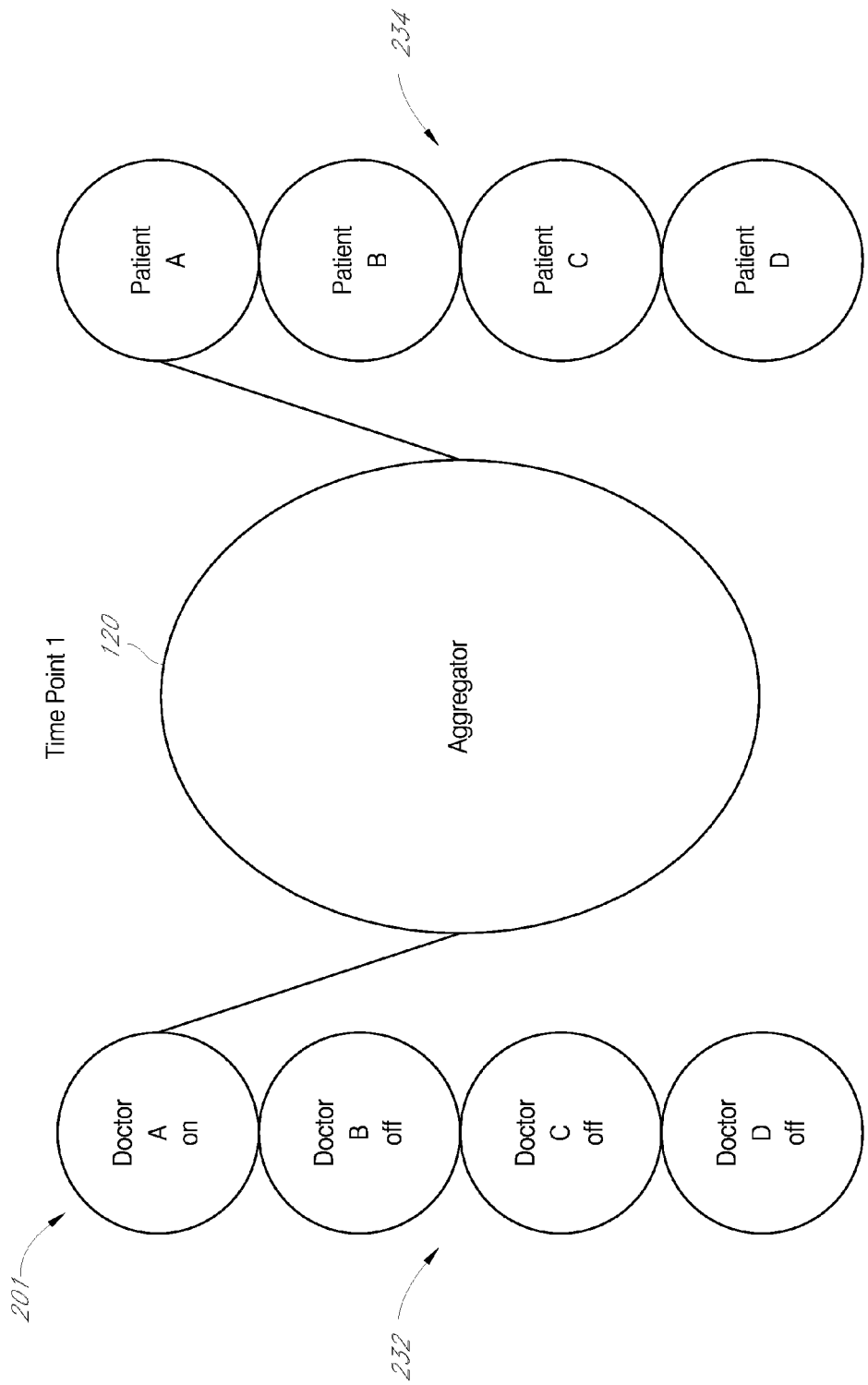
Figure 2C:
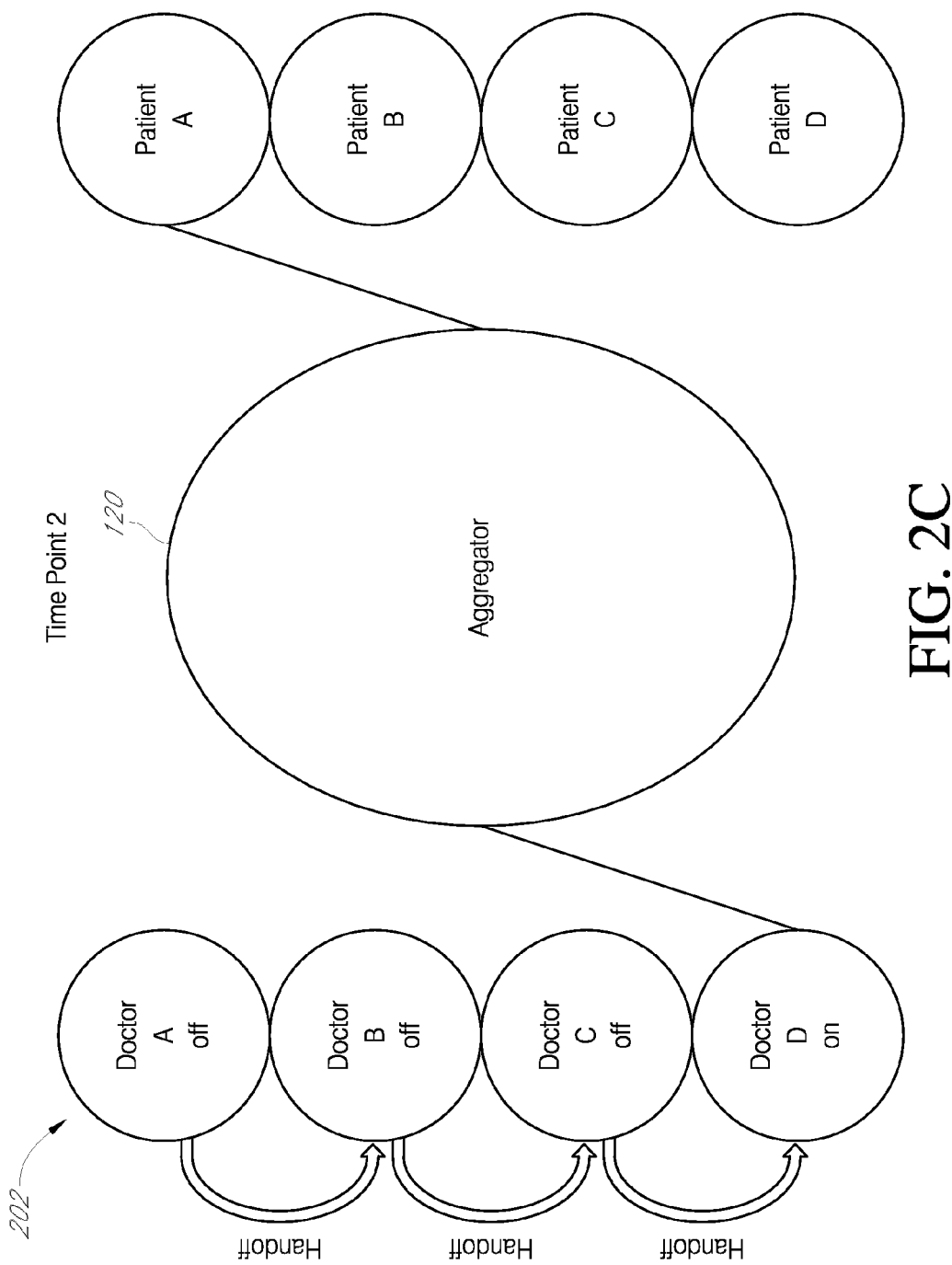

To briefly explain example operation of the aggregator 120, an example handoff and message router scenario is provided in FIGS. 2B and 2C. Suppose at Time Point 1, Doctor A is in charge of care for Patient A (FIG. 2B). Subsequently doctors change shifts, and Doctor A hands off Patient A to Doctor B, who hands the patient off to Doctor C, who hands the patient off to Doctor D. So at Time Point 2, Doctor D is in charge of Patient A. If Doctors A-D use the aggregator 120, this system can keep track of the symbolic links between each doctor and Patient A, dynamically aggregating them and being aware which doctor is in charge of Patient A at any one time (FIG. 2C).

Suppose that Doctor A orders a medication and makes an error. A pharmacist, who processes the medication order at Time Point 2, can use the current system to know that Doctor D needs to be informed of the error. The pharmacist does not have to go through the lengthy and inaccurate process of consulting the inpatient unit board to find out who the physician in charge of Patient A. Because, in several embodiments, the aggregator 120 uses input directly from the doctors to register hand-offs in real time, the aggregator 120 is inherently more accurate than the manual process used by the unit clerks, which relies on doctors' work schedules.

Figure 2D:
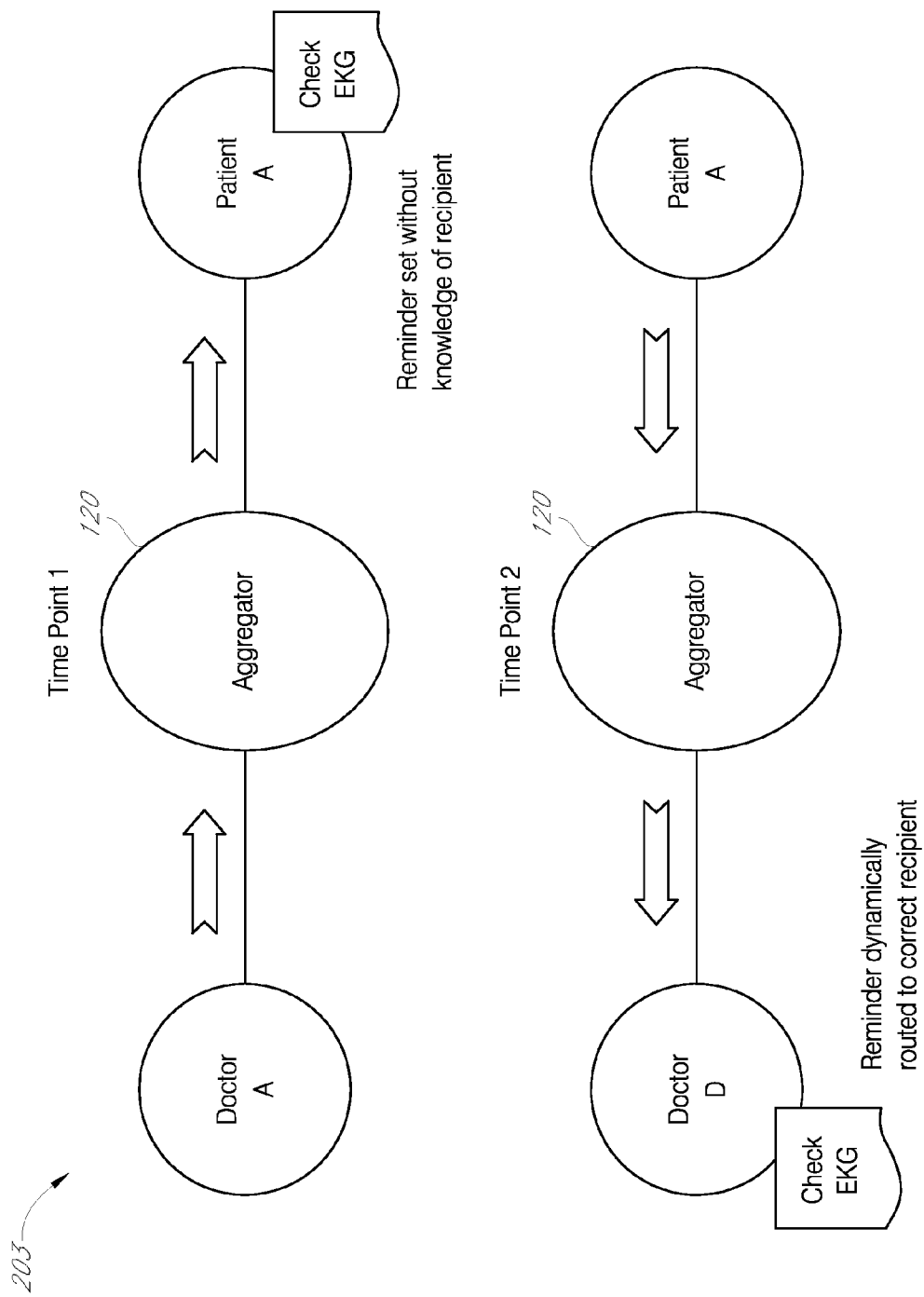

Taking one step further in FIG. 2D, suppose Doctor A at Time Point 1 orders a test which requires some time to complete (for example an electrocardiogram (EKG)—a test of electrical activity of the heart). Let Time Point 2 be the time when the EKG is complete. As with most tests, the interval between Time Point 1 and Time Point 2 cannot be precisely known (e.g., EKG can take various times according to the schedule, staffing and load of the EKG lab). Therefore, Doctor A cannot prospectively determine at Time Point 1 who would be the doctor in charge of Patient A at Time Point 2. However, the aggregator 120 can reliably calculate that it can be Doctor D, because it dynamically determines it at Time Point 2 (FIG. 2D). Therefore, using the aggregator 120, Doctor A can set a reminder to check the results of the EKG without explicitly specifying its recipient. The reminder can be timed or triggered by arrival of EKG result or by the presence of an abnormal result. The aggregator 120 can route the reminder automatically to the doctor in charge of the patient when the reminder is triggered (e.g., at Time Point 2 the reminder is routed to Doctor D).

Figure 3A:
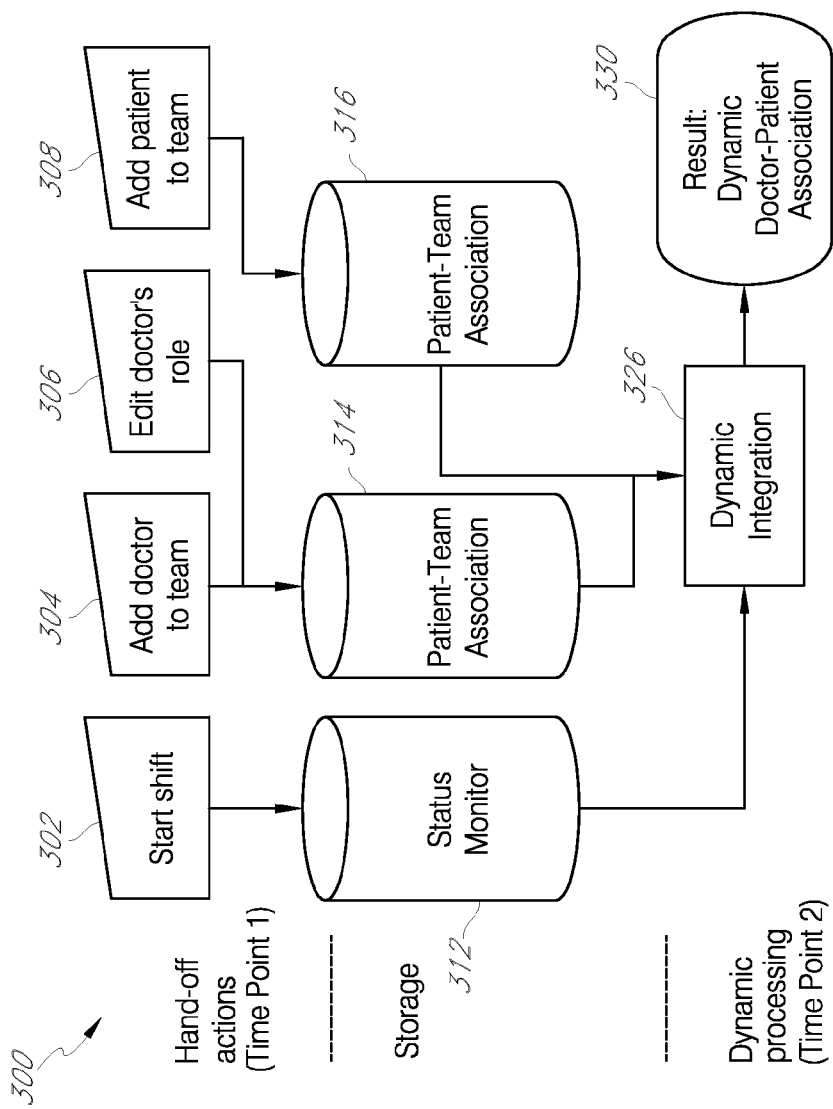
FIG. 3A illustrates example components and features of the aggregator system.

Referring to FIG. 3A, the aggregator 120 can allow healthcare providers to (among other things) 1) sign in and sign out of the aggregator 120 (block 302—start shift), allowing the aggregator to monitor the state of the provider (using a status monitor database 312 or the like), 2) to indicate their affiliation to a group of other providers, a team (block 304—add doctor to team), 3) to assign a patient to the team (block 308), to subsequently edit such assignment (e.g., block 306), 4) to perform integration, on demand, of the collected information for any patient (block 326) with the result (330) of displaying which provider is responsible and available to take messages at any one time.

In several embodiments, the aggregator 120 can maintain the database 312 to store the status of the provider. This database 312 can be optionally queried to retrieve information indicating whether the provider is present or absent from the healthcare facility, and/or is available to take messages by pager or other means (for example the provider is on-call). This status database 312 can be used to aggregate timing data to assess the provider's job performance and compliance with regulatory requirements (such as provider work hours limitations according to the American College of Graduate Medical Education).

In several embodiments, the aggregator 120 can also maintain a table 314 or database of doctor-team associations, which corresponds to the table of doctor links 222 described above. Similarly, the aggregator 120 can maintain a patient-team association database or table 316, which corresponds to the table of patient links 224 described above. In one embodiment, the aggregator 120 uses the tables 314, 316 to determine doctor-patient relationships based on their respective team affiliations.

Figure 3B:
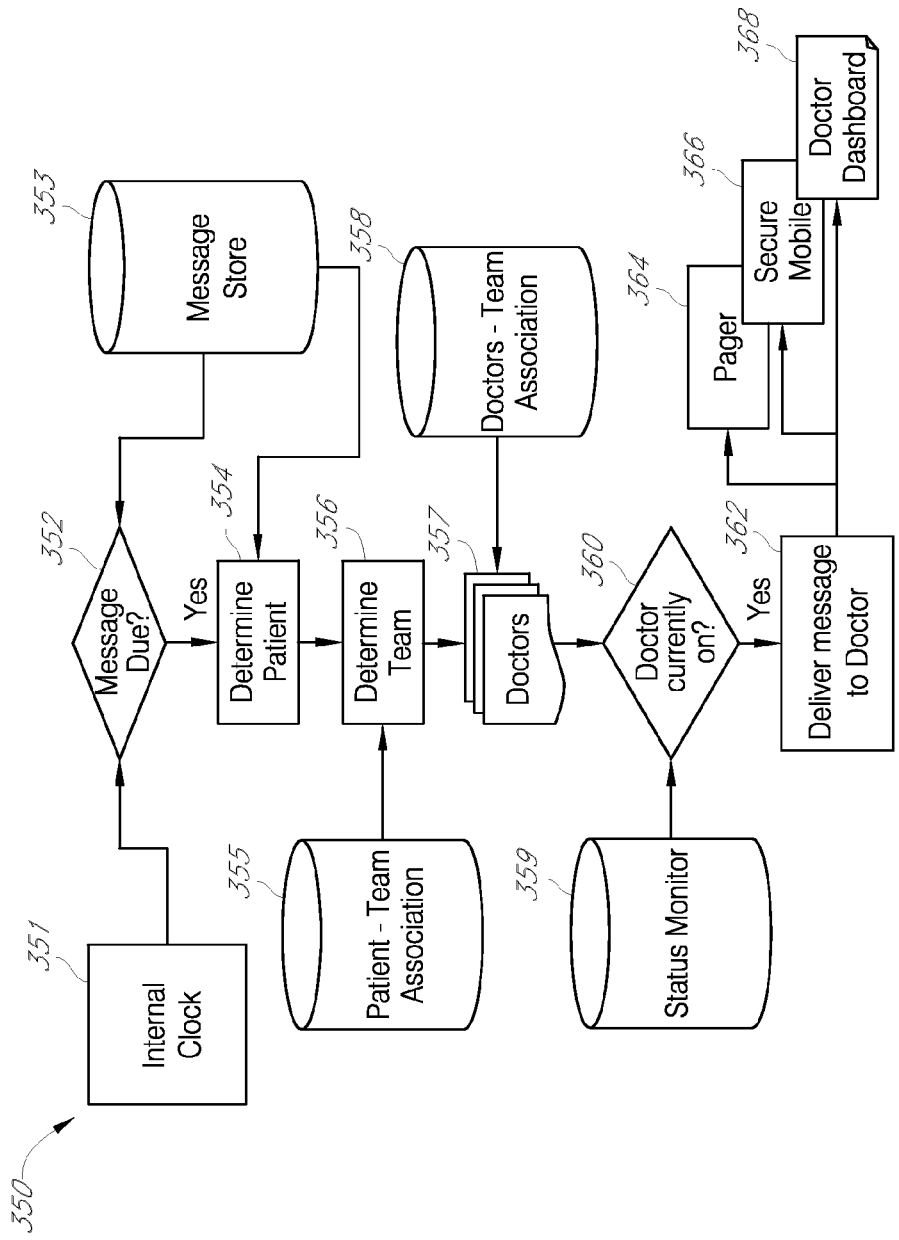
FIG. 3B illustrates an embodiment of a messaging process that can be implemented by the aggregator system.

Referring to FIG. 3B, an embodiment of a process 350 is shown for routing messages to the appropriate provider without having to know the identity of that provider beforehand. The process 350 can be performed by the aggregator 120, and more particularly, by the messaging component 124.

The process 350 begins at decision block 352, where the messaging component 124 evaluates whether a message is due. The message may have been created previously and is stored in a message data store 353. The messaging component 124 can compare a due date or deadline in the stored message with a value of an internal clock 351 to confirm whether the message is due. If it is not due, the process 350 waits. Otherwise, the process 350 proceeds to block 354, where the messaging component 124 determines a patient 354 with which the message is associated from the message data store 353.

At block 356, the messaging component 124 determines a team associated with the patient by consulting a patient-team association table 355 or the like. Once the team is identified, the messaging component 124 can determine which doctors are associated with that team at block 357 by accessing a doctor-team association table 358 or the like. The messaging component 124 then determines whether a given one of those doctors is currently on duty at decision block 360. (The process of picking a particular doctor to contact from a team of doctors is described in greater detail below.) The messaging component 124 can determine this doctor status information by consulting the status monitor database 359. If the relevant doctor from the team is currently on duty, the messaging component 124 delivers the message to the doctor at block 362. The message can be delivered via pager 364, secure (or other) mobile communications 366, via a doctor dashboard 368 or similar display (see below), or the like. If the doctor is not available, the messaging component 124 can determine whether another doctor in the team is available, repeating blocks 360 through 362.

III. Example User Interfaces

FIGS. 4A through 14 illustrate various example user interfaces that can be generated by the aggregator 120 or components thereof. In several embodiments, a provider uses a web browser or other application to access these user interfaces. In addition to having its ordinary meaning, as used herein, the term "user interface" can also mean one or more screens or displays. Thus, the term "user interface" is used interchangeably herein to refer to a single display or screen of information and multiple screens or user interfaces. Further, several example user interface controls are presented herein for performing various features. It should be understood that these user interface controls are merely examples, and different controls can be used for the same features. For example, links are shown in some of the user interfaces, but such links could be replaced with buttons, select boxes, or the like, and vice versa.

Although not shown, the provider may be presented with a log-in screen, which requests user name, password, and optionally a biometric key or other credential. Alternatively, secure access can be performed via integration of the application in the Electronic Medical Record (EMR) application 104 using Active Directory (or other directory services) or other single sign-on methodology.

Figure 4A:
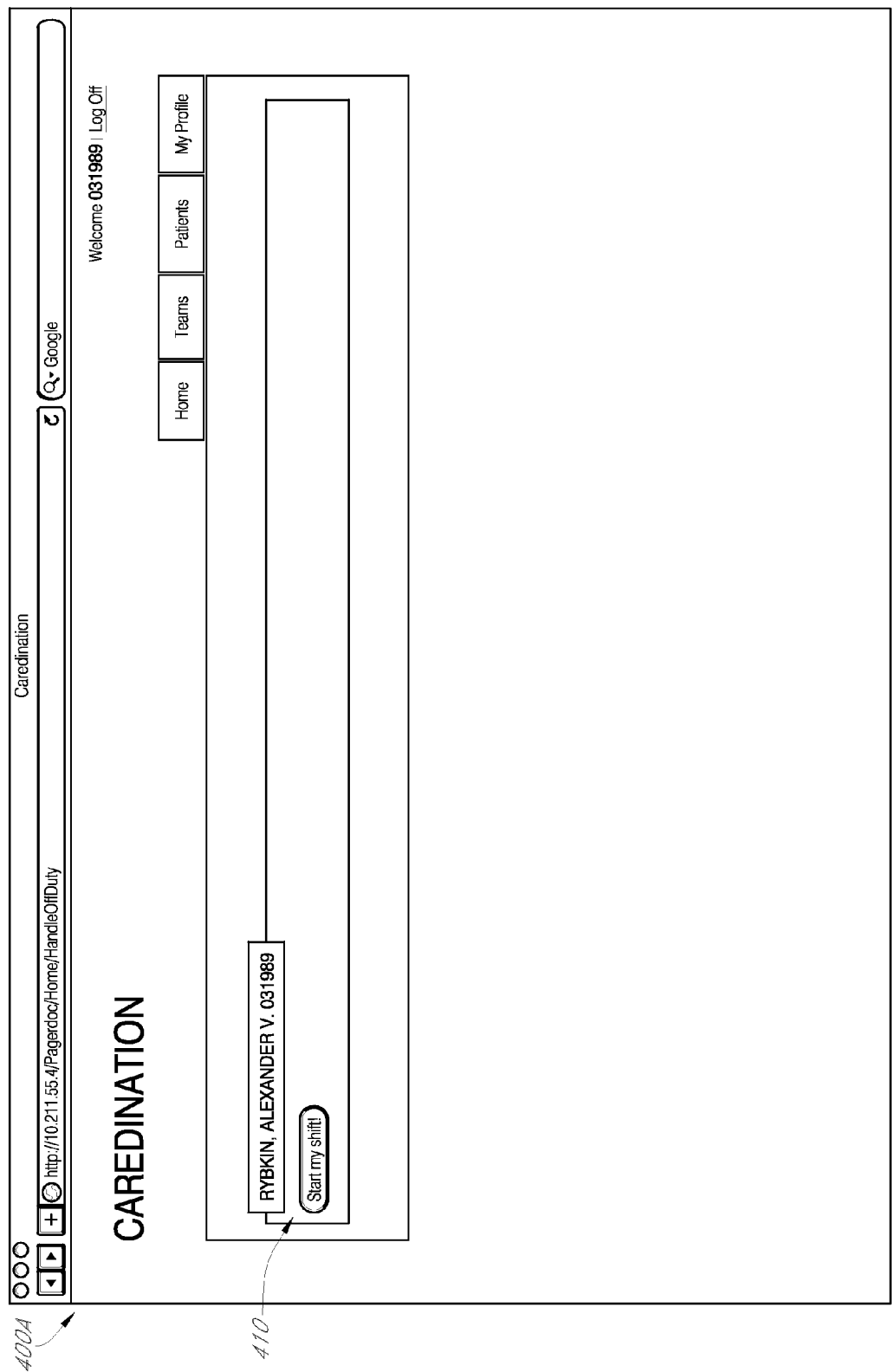

Once the provider is logged in, he may be presented with a user interface 400A shown in FIG. 4A. In this user interface 400A, a button (or other control) 410 is shown, which is selectable by the provider to enable starting his shift. Alternatively, the aggregator 120 may include a facility to start the provider's shift by detecting the presence of the provider by recognizing a biometric key, an access card, a hardware security token (such as a fob), by proximity detection technology (such as RFID), any other available authentication technology, combinations of the same, or the like. The aggregator 120 may also include additional controls, which would allow the provider to identify nuances of his status, for example, the provider may have ended his in-hospital shift, but remains on pager call from home.

Figure 4B:
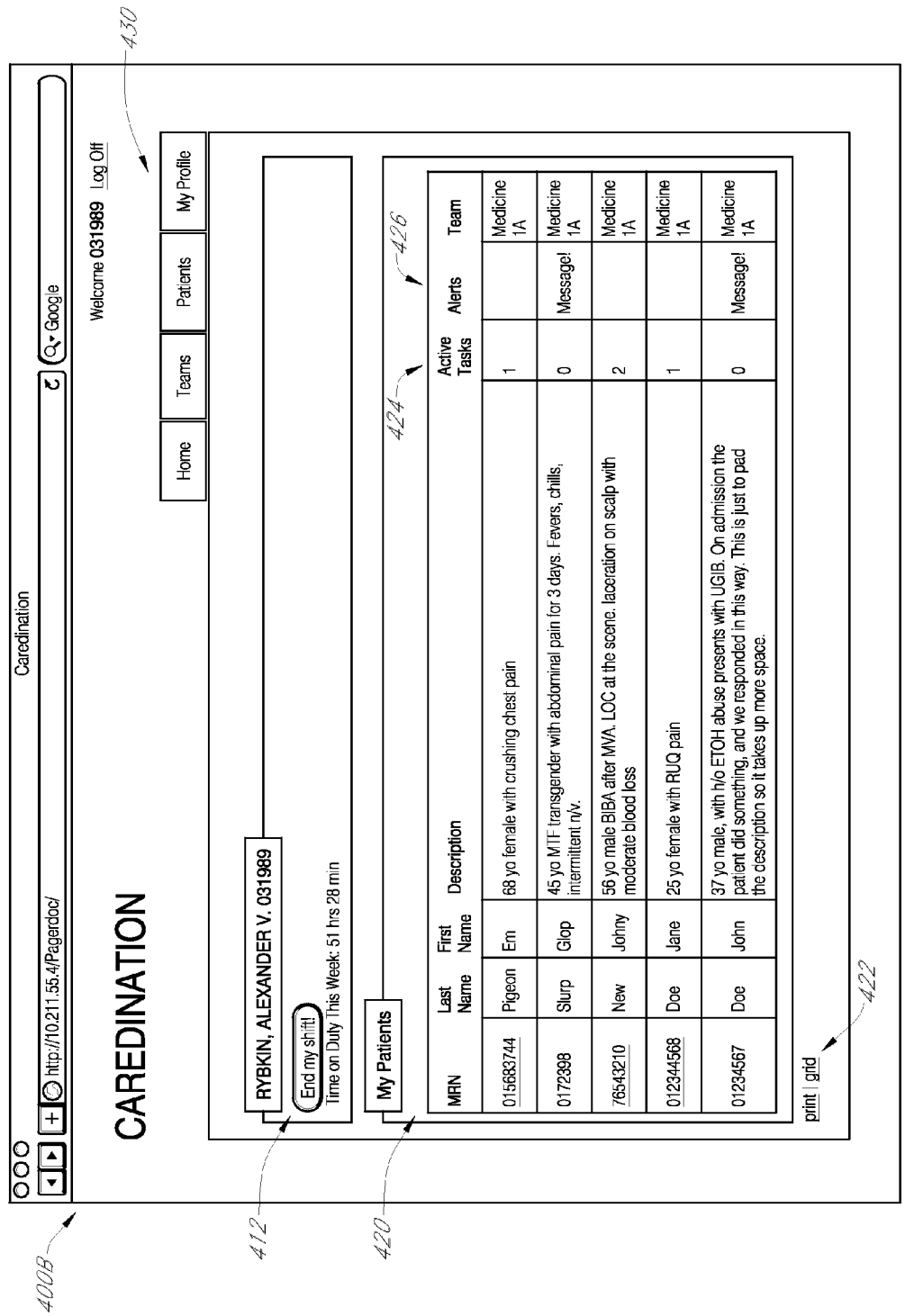

Once the provider has indicated to the aggregator 120 that he is on service, the aggregator 120 displays a list of his patients 420 in a tabular form, as shown in the user interface 400B of FIG. 4B. The list 420 includes the patients who are specifically assigned to the provider at that time. The list contains the patients' basic information, such as name, medical record number, and a brief description. In addition, the table displays alerts 426 about messages and notifications that have been sent about each patient, as well as reminders of tasks 424 to be performed. This patient table 420 allows navigation (through web links or other links) to a patient information screen (see FIG. 6—described below), which aggregates and allows editing of patient information, messages, tasks, and notifications.

The user interface 400B includes various controls 430 for accessing a home screen, team information, patients, and the provider's profile. The provider can control which patients are assigned to him by editing his team affiliation by accessing one of these controls 430, which results in display of an example team user interface 500 in FIG. 5A. The team user interface 500 lists the teams 510 of which the provider is currently a member. The provider can be a member of zero, one, or many teams. The team user interface 500 also lists (or alternatively has a facility to search and dynamically list) the teams 520 that can be added to the provider's team affiliations. The provider can select a team 520 and add it to his roster 510, or drop a team from the roster 510.

In several embodiments, the teams have patients assigned to them, so the relationship between the provider and patient can be mediated through teams. The providers can use the function of team affiliation for the purpose of patient handoff. For example, a physician who is going on or off duty can collectively reassign the patients on his team to another provider by removing himself from a team (control 514) and by the other provider adding himself to the same team. Alternatively, a provider can directly assign another provider to a team without having to have the provider assign himself to a team. This feature can be useful in teaching hospitals, where a teaching provider desires to assign a provider to a particular team. Advantageously, in some embodiments, teams allow the patient affiliations to the physicians do not need to be managed individually, making the process simpler, more convenient and less error-prone. Additionally, since more than one physician can be on a team at any one time, status information, gathered by the aggregator 120 at login, can be used to identify the doctor on the team who is currently on duty and available to receive communications. In the depicted embodiment, controls 512, 522 are also provided for editing and viewing details of teams, and a control 526 is provided for creating a new team.

The providers also manage the connections between patients and teams. Typically in an inpatient setting, a patient can be associated with a team at the time of hospital admission. The patient is removed from the team at the time of discharge and is possibly reassigned to a different team to reflect the patient's affiliation with an outpatient provider. Further, a patient can be associated with more than one team, so for example, a patient may be affiliated with a primary inpatient team (e.g., family medicine admitting) and a consult or cross-cover team (e.g., cardiology consult).

Figure 5A:
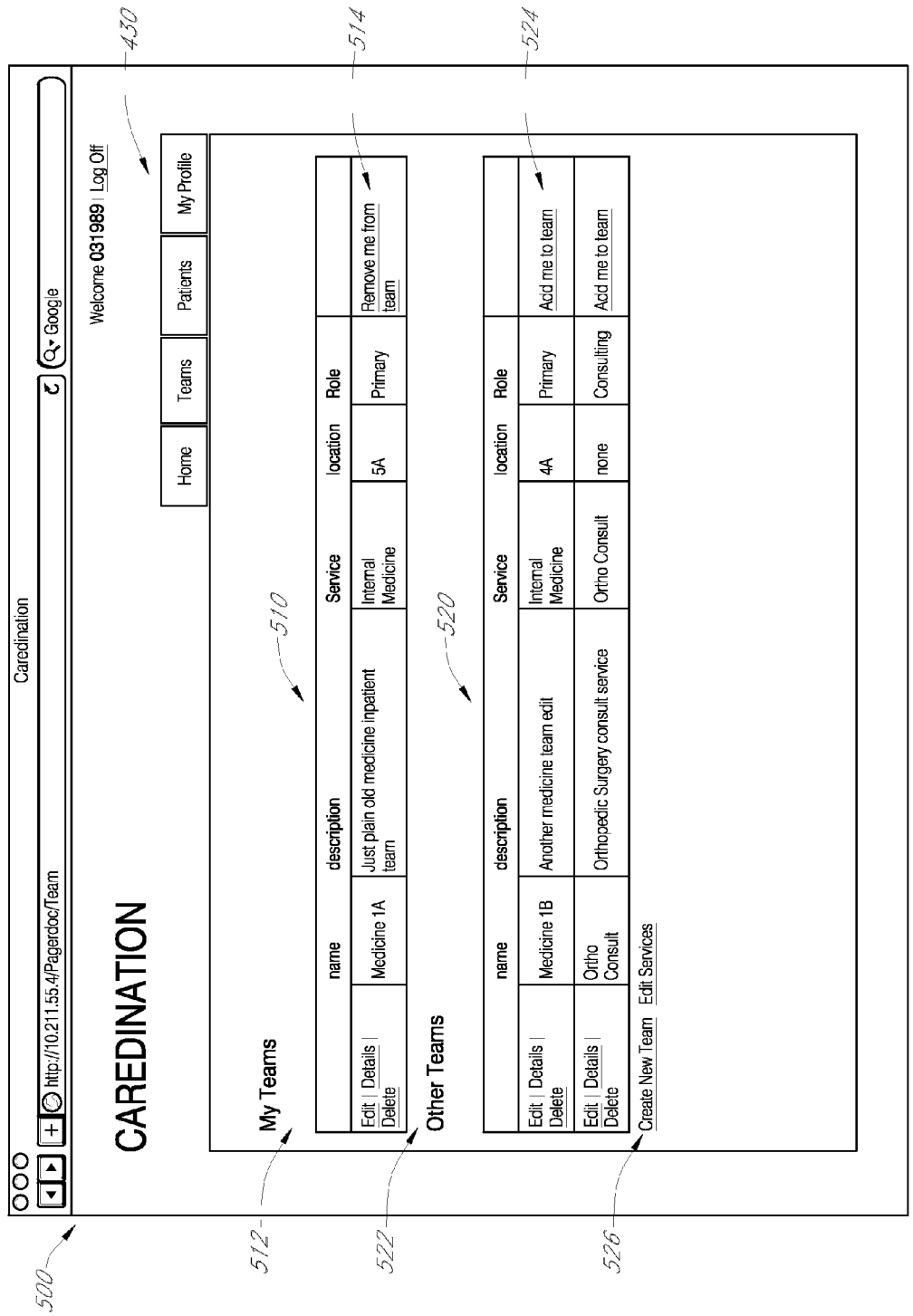
Figure 5B:
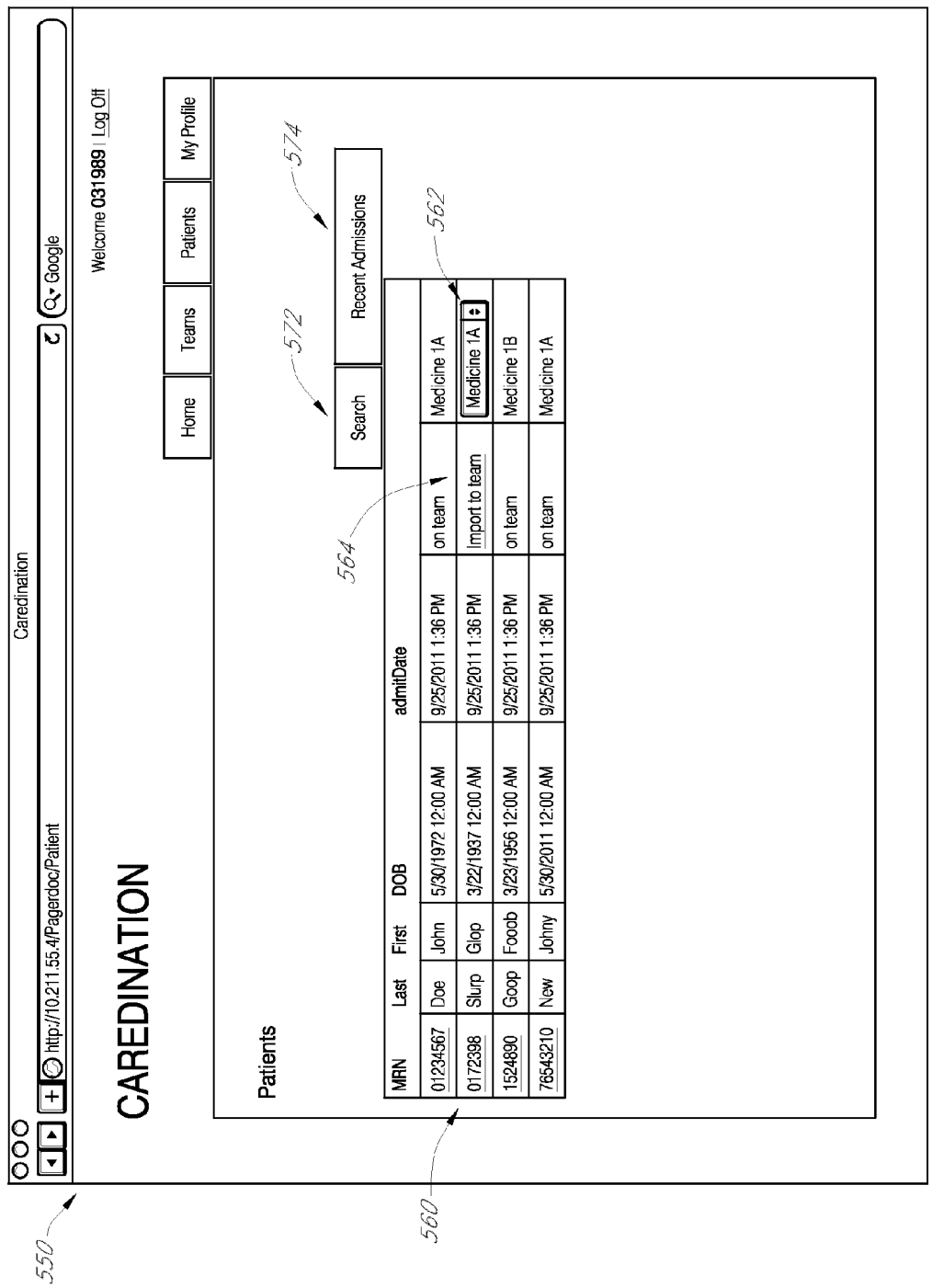

In an embodiment, when the patient first presents to or visits with the provider (or earlier), the provider associates the patient with his team using a patient user interface 550, as shown in FIG. 5B. The user interface 550 lists (or has the facility 572 or 574 to search and dynamically list) some or all available patient records 560 stored by the aggregator 120. The provider may generate a new patient record if the patient is new to the aggregator 120. Alternatively the list of patient and patient records may be imported from the Electronic Medical Record database 130 (for example using an HL7 ADT data feed). The list of patients 560 allows the provider import the patient to one of provider's teams. For example, in the depicted embodiment, a link 564 is provided for importing a particular patient to a team. This link can be provided for any patient not currently affiliated with a team. Other patients that are already on a team are shown with their team affiliation (e.g., "Medicine 1A"). A drop-down box 562 enables a user to select a particular team for a given patient not yet assigned to a team. In some cases, the user interface 550 may also be used to change a patient's team affiliation (see also FIG. 6A).

Figure 6A:
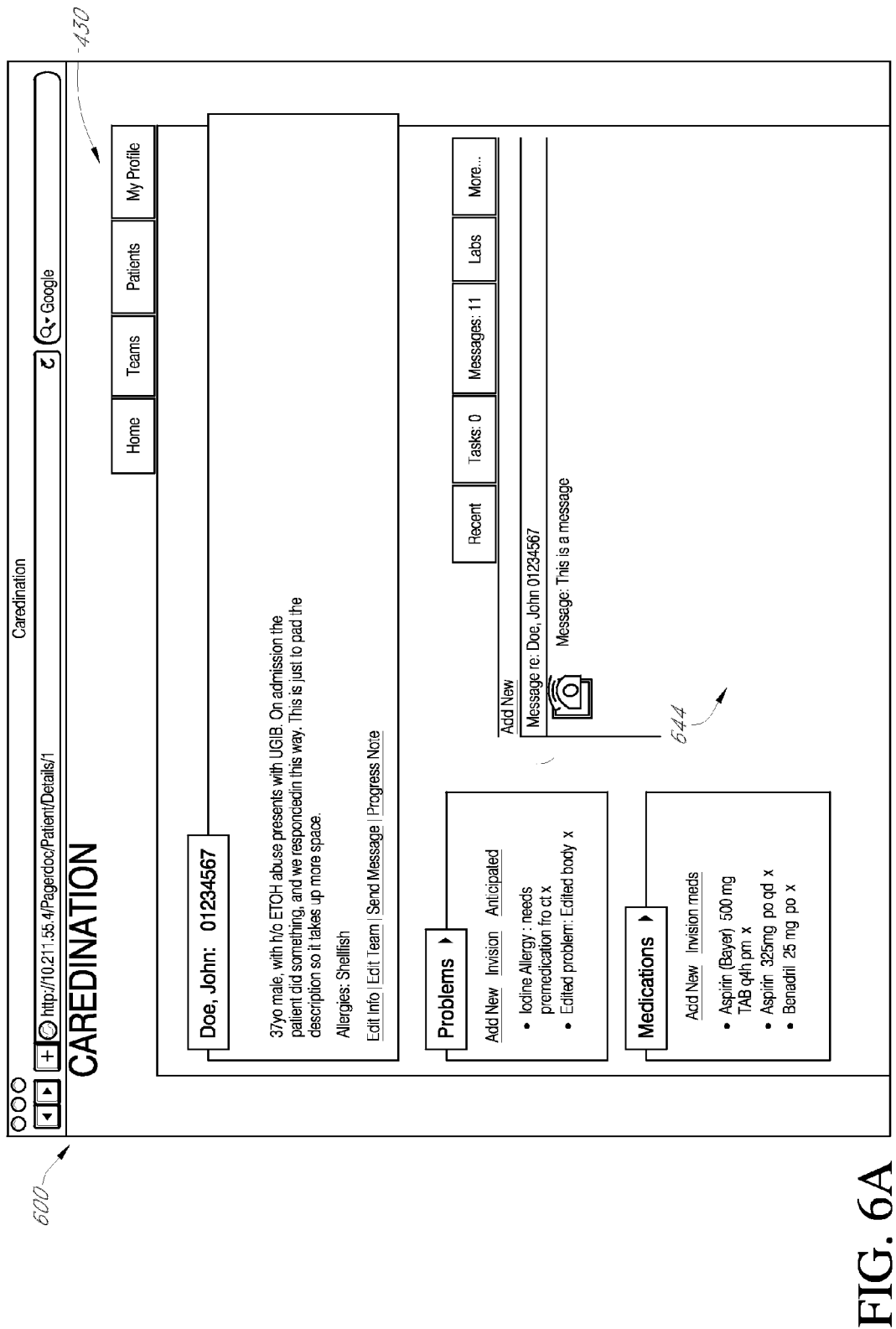

Subsequently, the provider can edit the patient's team affiliation by going to the patient information user interface 600A of FIG. 6A (link 615) (to which he can now navigate through the master patient list on the user interface 400B). The patient information user interface 600A has the facility to access the patient's roster of teams, to remove or add teams to this roster, via link 615. The provider can use this function when the patient is discharged from the hospital, in which case the provider removes his team from the patient's roster, thereby breaking the connection between himself and the patient. Alternatively, clerical staff can perform this functionality. The user interface 600A also displays general information 610 about the patient, including symptoms, allergies, biographical data, and the like.

Figure 7:
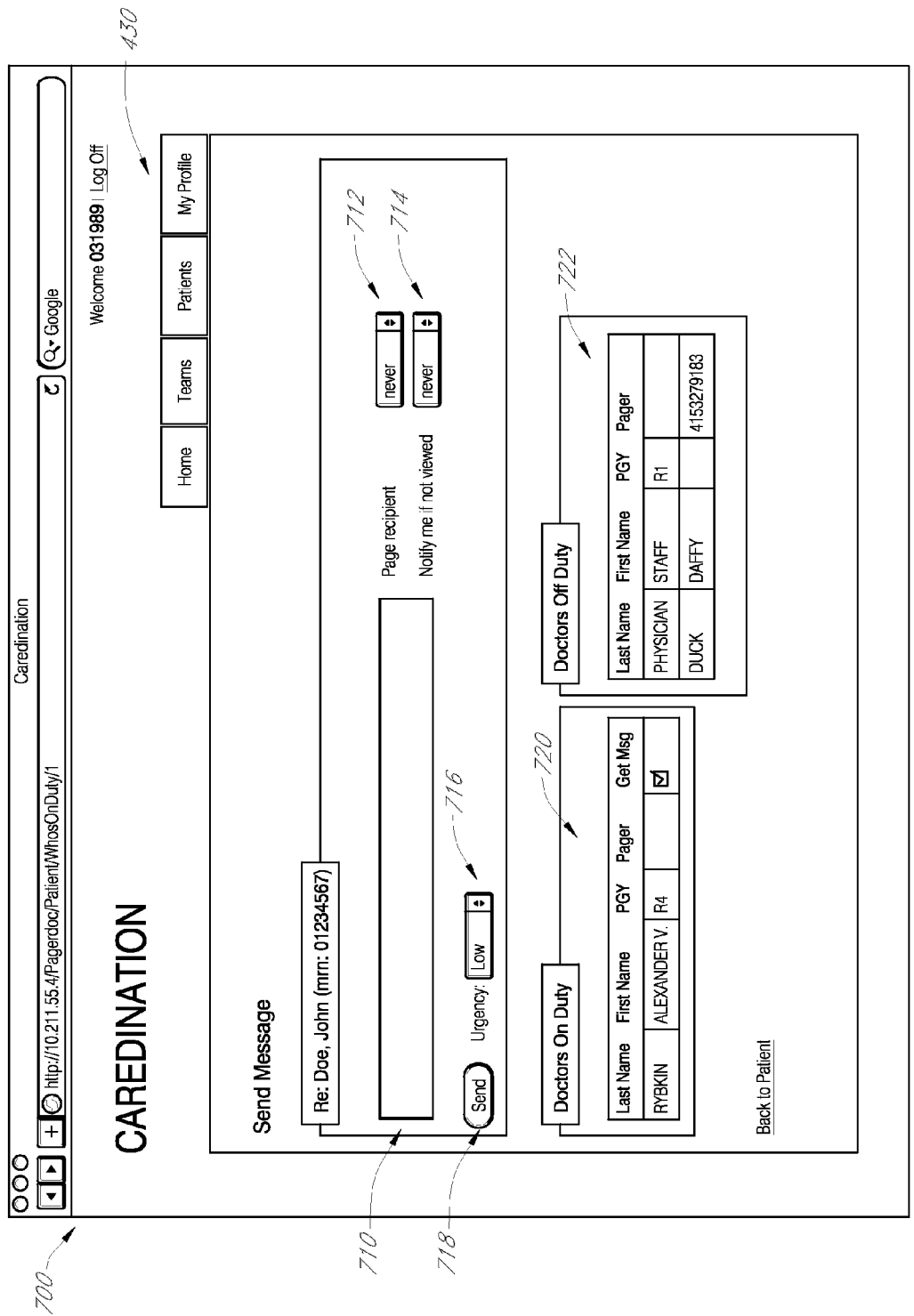

The patient information user interface 600A also has the facility to send messages regarding this patient to other providers, using link 617. This link takes them to a message user interface 700, an example of which is shown in FIG. 7. (Alternatively, messages are created within the user interface 600A). The message user interface 700 has a text field 710 for the text of the message. For other types of messages (described in more detail below), including comments, tasks, events, or the like, additional text fields may be provided. These fields can include a title field, a due date field (e.g., for tasks), and a date field (e.g., for events). Other fields or controls may also be provided. The message user interface 700 also contains the list of the potential recipients of the message. The aggregator 120 dynamically constructs the list of the potential recipients in one embodiment, taking into account the patient's team affiliations, the affiliations of providers with that team, the status of those providers (on duty, off duty, on call, etc), and optionally the team affiliation of the sender of the message (e. g. the current user). Each recipient on the resulting list can be selected or deselected by the sender of the message (using controls 720, 722), who thereby adds or removes the provider from the list of the recipients.

Optionally, the aggregator 120 may contain an algorithm to limit the recipient list based on the stated role of the provider, for example, the intern may be the provider to contact first, resident next, and attending physician last. When the user sends the message (e.g., using button 718), the patient information user interface for the listed and selected providers is updated to include the message, and an alert is placed on the patient master list on the front page of the application. Optionally, the message user interface contains the facility for the sender to specify the urgency of the message (e.g., Low, Medium, or High) using control 716. These alerts can be color-coded when displayed on the user interface 600A of FIG. 6A (or 600B of 6B; see below) with respect to the urgency of the message (e.g., green for Low, yellow for Medium, and red for High).

More generally, a first role can be assigned to respond to a message or task first, and a second role can be assigned to respond to the message subsequent to the first role, and so on up to as many people are included in a team. The messaging user interface 700 can provide functionality to prioritize messages or tasks in this manner. As an illustration, a first role can be a training role such as an intern or resident, while the second role can be a supervisory role such as a resident (for supervising an intern) and an attending physician. The messaging user interface 700 can allow the order of roles to be notified to be selected without selecting actual names of providers. In response to a patient being handed off to a new healthcare team, the aggregator 120 can determine the roles of the providers in the new healthcare team and send messages (at the proper time) to such providers accordingly.

If a person first assigned to receive a message or task does not respond within a certain period of time (which may be defined by the message initiator on the messaging user interface 700), the second person assigned to receive the message subsequently can be notified. Further, the messaging user interface 700 can include a control(s) for the first person to indicate whether the message was acted on. If the message was not acted on (e.g., which can be determined by evaluating that the first person did not use said control(s)), the message can be escalated to the second person assigned to receive the message. In this manner, supervisors can follow up on and monitor the actions of trainees. Outside of the teaching context, this escalation functionality can be used by supervisors to monitor subordinates. The aggregator 120 can also reduce errors in teaching hospitals by virtue of this escalation feature. More generally, this escalation feature can reduce errors in any hospital or clinical setting.

The message user interface 700 also contains a select box control 712 that enables optionally paging the recipients presently or at some time in the future. If this control 712 is chosen, the aggregator 120 connects to the paging provider 180 (FIG. 1) and places a page electronically. The messages sent through the non-secure paging system may include the notifications that a message is available to be viewed, and the user may log in to the secure portal to view it. Alternatively, the aggregator 120 may have the capability to send messages through other means, such as email or Short Messaging Service (SMS) through secure or non-secure means (e.g., block 170 of FIG. 1). The aggregator 120 may also publish an Application Programming Interface (API), through which an (optionally secure) client application may connect and receive messages or notifications (example client applications are described below).

In the depicted embodiment, the message user interface 700 also contains a select box control 714 that enables the user to request a notification in the event that nobody looked at the message within a selectable time frame. This notification can be another message, which the aggregator 120 automatically sends to the sender of the original message if certain conditions are met (e.g., if the specified time interval has elapsed and/or the message was not accessed by other providers). This notification can be a fail-safe mechanism for communicating desired health information, which allows making sure that a high-priority message is received. The recipients have the option to identify to the aggregator 120 that they viewed the message, thereby providing a return receipt, which may not directly sent back to the sender, but may be stored in a database. The aggregator 120 can also identify to the original sender whether the recipient viewed or accessed the message but did not act on it.

Messages may take various forms. Message subtypes may include (but are not limited to) comments, questions, tasks, events, problems, medications, and allergies. Many other subtypes are possible. By representing various forms of medical data as messages, the aggregator 120 can utilize its capacity for dynamically routed reminders, notifications and actions to make medical data more interactive. For example, when recording a potentially harmful medication in the aggregator 120 (as a message subtype), a provider can set a dynamically routed reminder for someone in the future to check labs or otherwise monitor for expected complication.

Messages can have a standard core of functionality, including capability to store the sender, patient, title, body text, timestamp, and associated notifications (or other actions). One possible feature of messages in several embodiments is the ability to have child messages. The parent-child hierarchy of messages enables providers to use messages to create electronic conversations, as seen in FIG. 6A. For example, a first message 634 is shown, to which a second message 640 (indented below) is shown in response, as a child message. The messages shown are short and provided in a blog, microblog, or social networking format. In other embodiments, messages can be presented as instant messages, chat room messages, combinations of the same, or the like. However, the messages need not be in such formats in some embodiments. As another example, a provider may record a medication as a message; then, another provider may attach another message to the first in the form of a question. Subsequently a comment can be attached to the question, so that the whole team can see the answer. A provider who asked the question can even set a notification to himself if the question was not answered in the appropriate time frame. In several embodiments, this electronic conversation captures in an asynchronous manner the dynamic exchange of information and ideas among multiple providers involved in the care of a single patient. This approach goes beyond the current state of the art embodied in the typical electronic health record, which statically conveys data. The electronic dialogue described herein can contribute to a high level of coordination and integration of care. More generally, the aggregator 120 can provide healthcare providers with tools to create a dynamic asynchronous conversation or dialogue about the care of a given patient, enabling enhanced coordination and integration of care delivery.

Several examples of message subtypes follow. A comment can be a subtype of message, which does not have a specific recipient (recipients), but can be displayed to all members of the team. An event can be a subtype of message that is similar to a comment, but has a specific date associated with it. It can be used to record a desired event in the hospital course, such as an operation. A task is a type of message that has a due date, has a special status (complete or incomplete), can be made complete by user actions, and has a specialized set of actions.

Figure 6B:
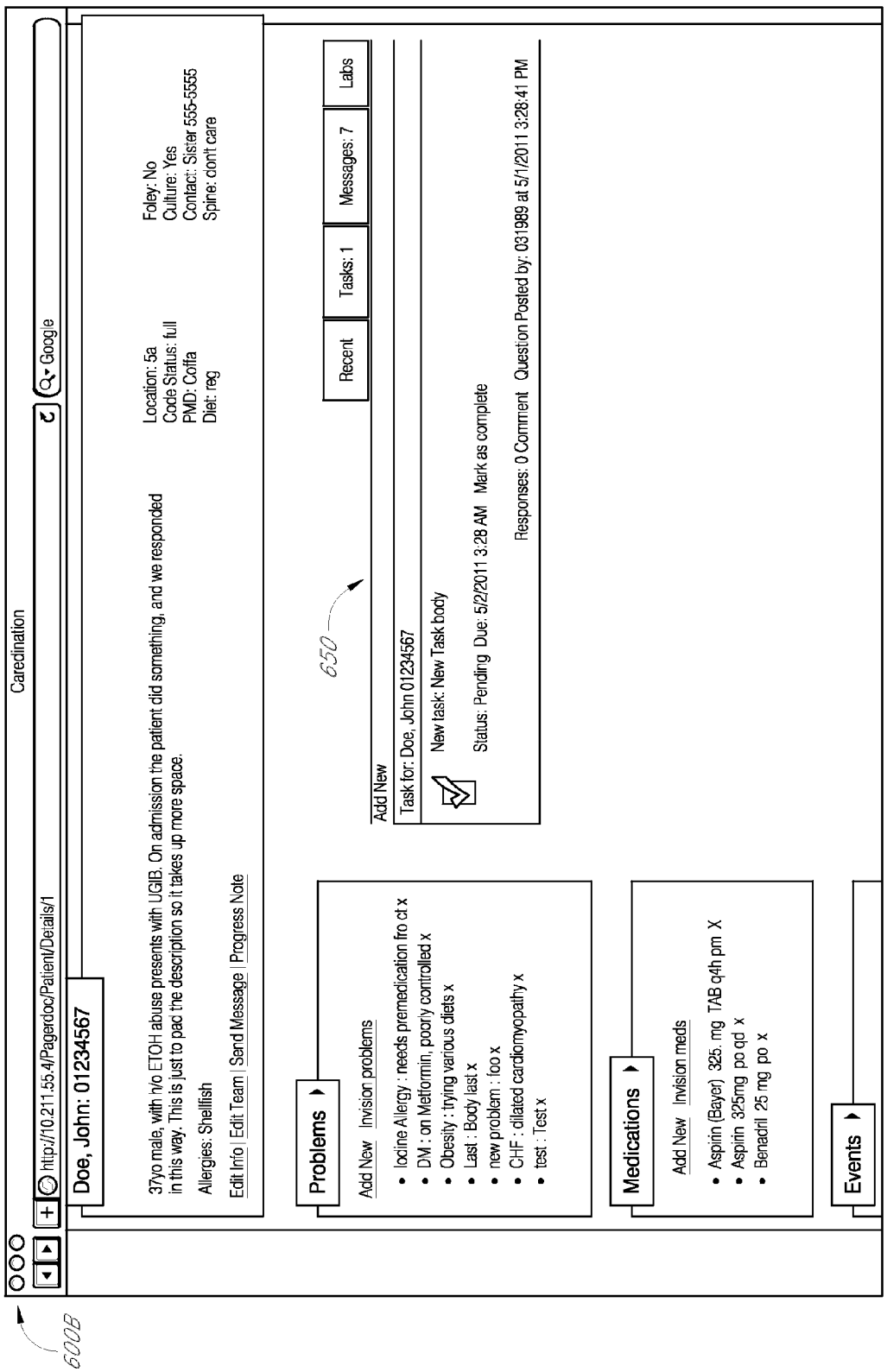

For example, referring to FIG. 6B, the patient user interface 600B includes a task 650. When a task is set, the provider who creates it (author), sets the task for the whole team (or optionally for a subset of a team). The author can specify the date and time when the task becomes due (see, e.g., FIG. 6B). The author can set a notification to be sent when the task becomes due to the provider who can be responsible for the patient at that time (to be dynamically determined by the aggregator 120 at that time). The author can also send notification to himself if the task is overdue for a certain period of time. For example, an attending may assign a task to a team of residents. She may not know prospectively who the responsible provider can be when the task can become due, but the aggregator 120 can dynamically determine that and can send the notification to the appropriate recipient. The attending may also specify that she should receive a notification if the task is not completed within one hour of being overdue. At that point in time, the aggregator 120 can evaluate the specified conditions (e.g., Is the task overdue? Is the task complete? Has it been more then one hour since the task became overdue?), and can send a notification to the attending if the conditions are met.

A notification for a message is an example of an action, which in a more general form that may be reused throughout the aggregator 120. An action can be a process that is automatically performed by the aggregator 120 and can involve sending a message (but is not inherently limited to sending messages), scheduling by the user for some time in the future, and automatic triggering at a predetermined time and/or by satisfaction of specified conditions. The usefulness of the actions can be greatly enhanced by the aggregator's 120 capability to dynamically determine the providers who are in charge of the patient at the time when the action is triggered. This function determines the recipients of the messages sent as a result of the action. The concept of an action can enable the aggregator 120 to schedule some kinds of messages to be provided at a future specified time or date. A provider might want to send a message conditionally, for example, based on the internal clock (see FIG. 3B) or on another condition (e.g., arrival of an abnormal EKG result). Each message type can specify a number of actions that a user can set, together with the options and logic that is specific to the action.

In one embodiment, the aggregator 120 provides a scripting interface with an API that allows definition of actions outside the source code of the aggregator 120. This API may allow dynamic message creation, sending, response, or adjustment to occur. For example, a comment message may specify the action to page a person to be dynamically determined, based on the input of a "Page recipient" select box (e.g., in 6 hrs, 12 hrs, etc.), if this input is other than "Never" or "Now." The comment message may also send a message with a page to the author of the message if the message has not been viewed by another user in the time frame based on an input to "Notify me if not viewed" select box, unless it's "Never." A "Question" message may specify an action to notify the sender if somebody answers the question by creating a child message, or alternatively if somebody does not respond in a particular time. A "Task" can have an action to remind the dynamically determined provider that a task is coming due. It can also specify that a message be sent to the originator of the task if the task is overdue by a certain time, among other features.

The aggregator 120 is capable of filtering messages by type, date, author, recipient and other parameters (among other criteria), allowing the aggregator 120 to dynamically generate a view of the current issues in the patient's care. This view is displayed on the patient information user interface 600A. In one embodiment of the patient information user interface, problems 620, medications 622, and events 624 (such as labs, operations, room transfers, etc.) are separately displayed on the left of the user interface 600A, and a running table 630 of the most recent messages and conversations can be displayed in a hierarchical fashion on the right. This arrangement is merely one example implementation, however. Additional tabs 632 allow display of tightly filtered messages, such as recent tasks, incomplete tasks, messages awaiting acknowledgement, labs, and the like.

Figure 8:
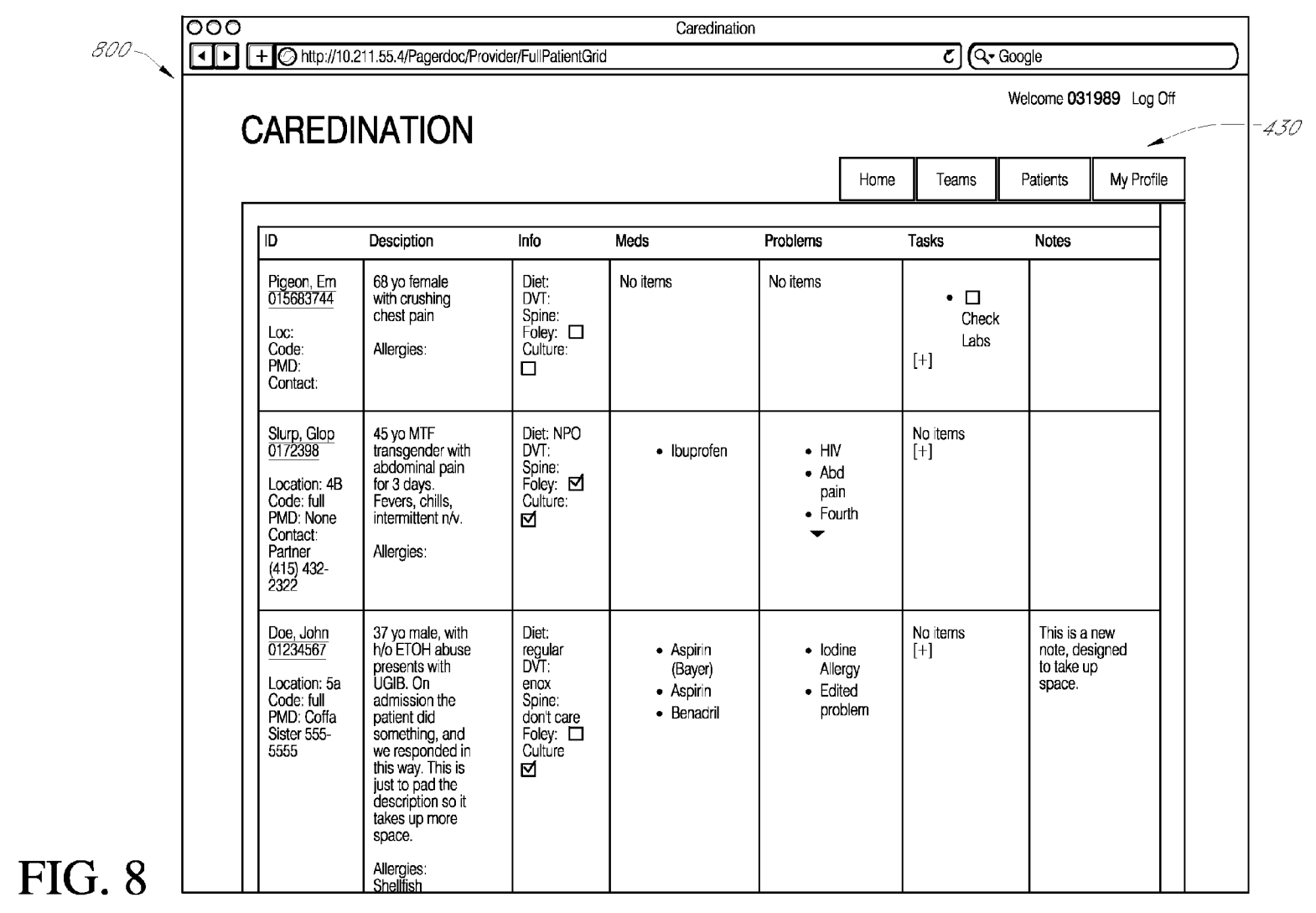

Messages can be formatted, along with supplementary information, into grids, which providers commonly use in patient handoff. An example grid 800 is shown in FIG. 8, which may also be accessed from link 422 of the user interface 400B (FIG. 4B). Providers often print grids on paper and use them as guides when signing out verbally to the provider coming on duty. The grids 800 in the current system can be used in a similar fashion, either in the printed form or displayed on a mobile device, such as a tablet, smart phone, computer, or other device. The client devices can also be used concurrently to receive and send messages and notifications.

The configuration of the patient grids 800 and patient information user interfaces 600A, 600B can vary based on the type of team to which the patient and provider belong. Multiple pre-defined templates are predefined and used to tailor display of data to the specific needs of the providers. For example, the information display for pediatric patients can substantially differ from the display for a OB/Gyn patient in Labor and Delivery.

The patient information user interfaces 600A, 600B and the grids 800 can be formatted and messages filtered appropriately based on the role of the user. The aggregator 120 can support multiple roles, such as provider, nurse, nurse practitioner, technologist, and manager, among others. Nurse and technologist roles may not have access to all the information accessible to providers in some embodiments; on the other hand, providers may wish to filter out nurses' or technologists' messages for the sake of clarity. The role system implemented by the aggregator 120 in some embodiments enables tight access control of patient information on the need-to-know basis, to aid compliance with confidentiality regulations concerning protected medical information (such as HIPAA). The role system can also enable the patient to access this system as a user. The aggregator 120 can present an appropriately filtered subset of information, appropriate for the patient. The patient would be able to ask the providers questions about particular medications or problems. Such an arrangement would improve the providers' awareness of patients' concerns, and thereby promote patient safety and satisfaction with care.

Figure 9:
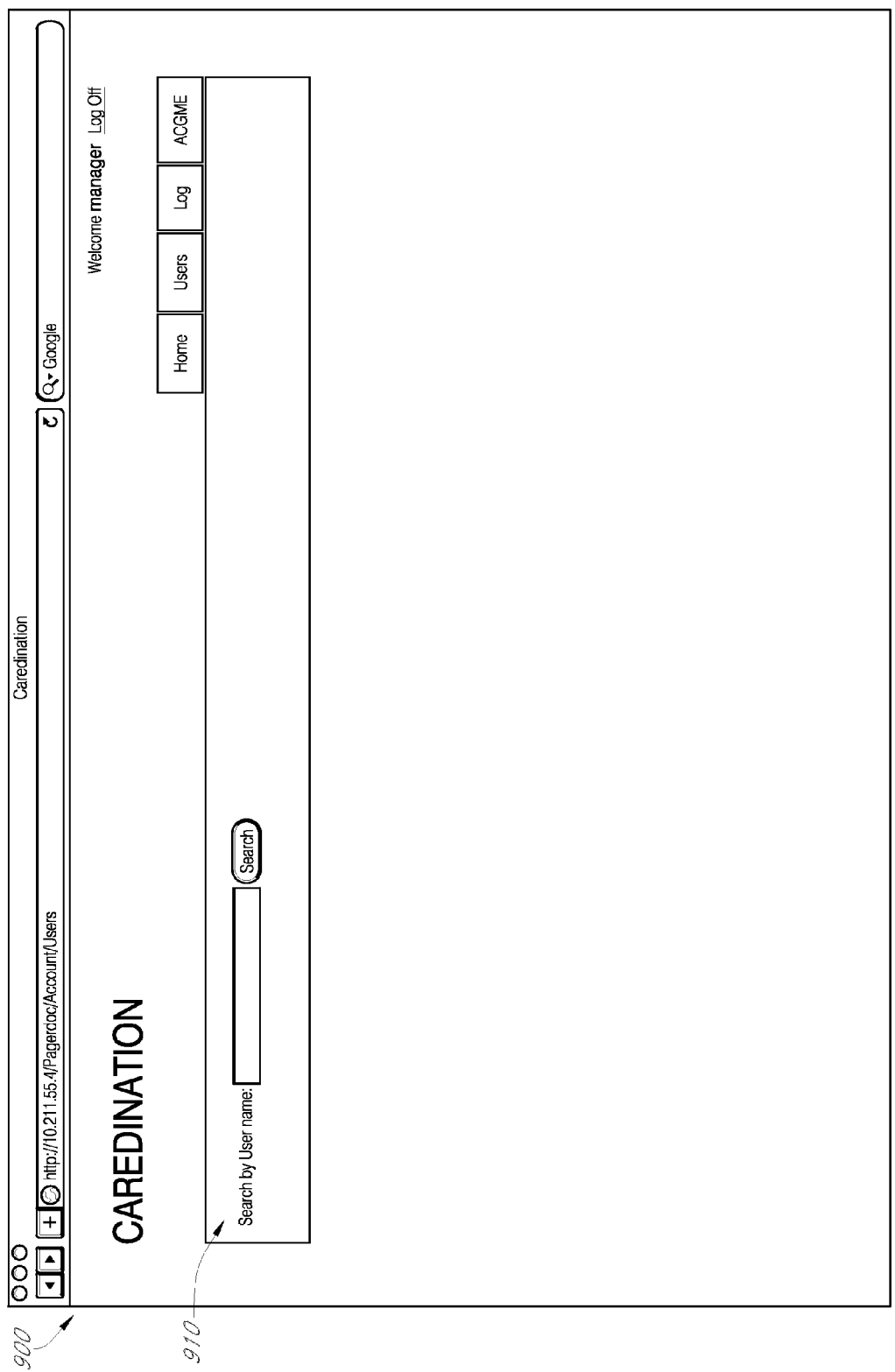

The aggregator 120 may also include a number of manager/administrator functions, which allows creation and management of user accounts and assignment/administration of user roles. The aggregator 120 is capable of using the stored data to display information, which is relevant to healthcare administration and regulatory compliance. For example, FIG. 9 illustrates an example management user interface 900 that allows a manager to search for users via search box 910. Upon searching for a user, a user interface 1000 of FIG. 10 can be presented to the manager. This user interface 1000 depicts various users 1010, such as providers, in a facility. Another management user interface 1100 shown in FIG. 11 can be accessed by selecting any of the users 1010 in FIG. 10. This user interface 1000 includes log information 1110 regarding the selected user, which includes logon and logoff times to the aggregator system.

An administrative dashboard 1200 in FIG. 12 may reflect the clock-time information for providers, aggregated from the log information 1110 shown in FIG. 11. This information can be used as evidence of healthcare facility compliance with American College of Graduate Medical Education (ACGME) work-hour rules. Alternatively, the aggregator 120 may contain a dashboard, which displays the census of patient on various services and teams. This information can by used by the administrator to balance work load among teams and physicians, improving efficiency of service and job satisfaction for providers. In one embodiment, the compliance module 126 of the aggregator 120 compiles this work-hour information or other information and automatically sends it to the ACGME or another regulatory agency.

Figure 13:
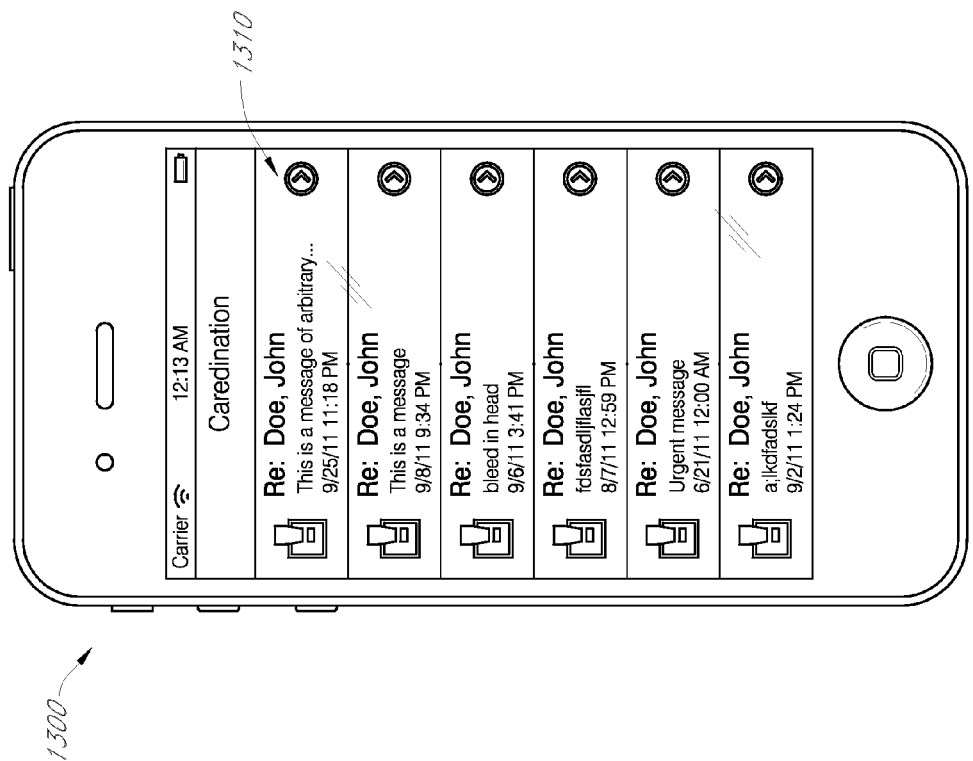

FIG. 13 illustrates an example user interface 1300 that can be implemented in a handheld device, such as a wireless phone, smartphone, tablet computer, PDA, or the like. Although any of the above-described user interfaces can be implemented on such a device, it can be helpful to condense the amount of information provided on such a device for readability purposes. Messages 1310 are shown in a condensed format in FIG. 13. These messages 1310 can have some or all of the content of the messages described above, including different message types. The aggregator may use "push" or "pull" notification technology to notify the handheld device and user of the arrival of messages. The messages 1310 are presented in a list format, although different formats can be used.

Figure 14:
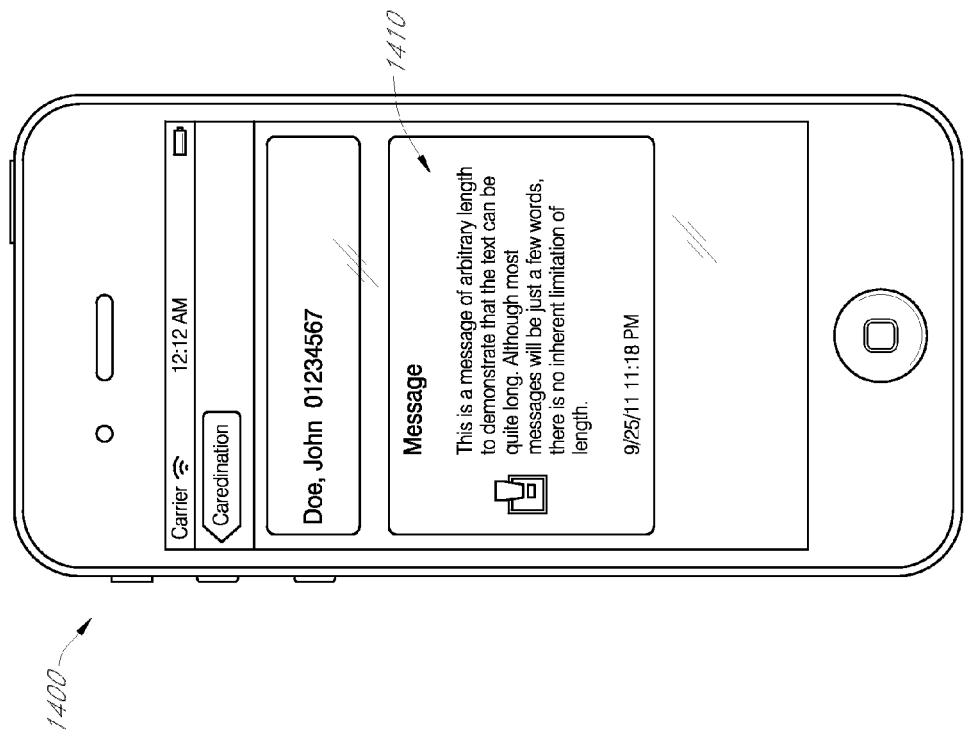
Figure 16:
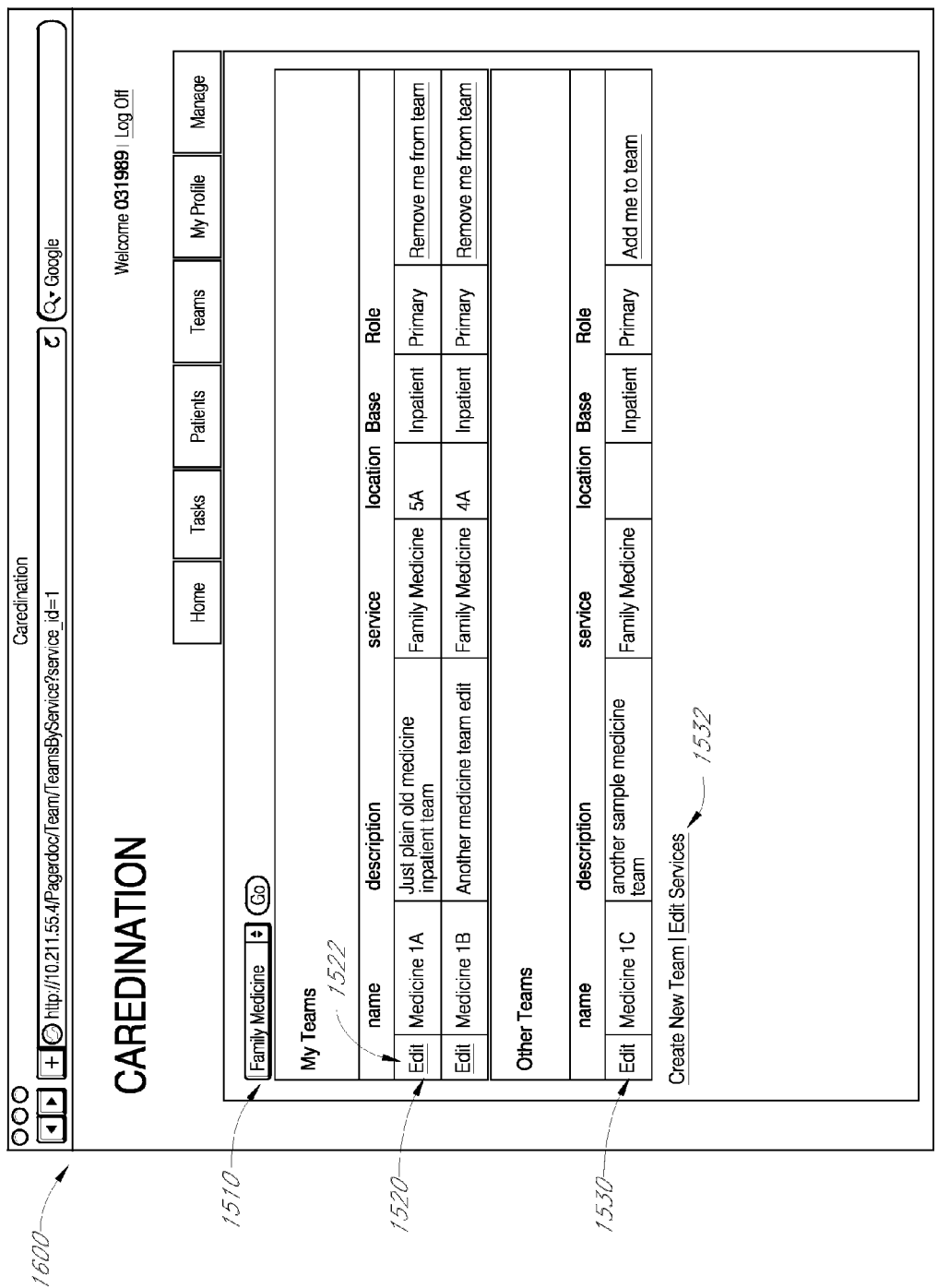

FIG. 14 illustrates another example user interface 1400 that can be implemented in a handheld or similar device. The user interface 1400 depicts a message 1410 in more detail. The message 1410 shown can be displayed in response to a user selecting one of the messages 1310 in the user interface 1300 of FIG. 13. Other features described herein may also be implemented in a handheld or similar device.

IV. Service Embodiments

In another embodiment, the team concept described herein can be extended to encompass additional functionality. A team may include more than just providers from a single clinical facility in one embodiment. For example, a team can include any combination of providers or other personnel from multiple clinical facilities. As an illustration, a team can include an intern, resident, and attending physician from one facility, a pharmacist from another facility, a home care nurse, technicians from a lab facility, an independent contracting physician's assistant, and so forth.

In another embodiment, teams can be configured based on provider specialties. Providers or administrators can assemble these specialty teams, such as diabetes specialists, radiologists, cardiologists, and so forth. A provider going on vacation or otherwise becoming unavailable may wish to find providers to take care of his patients. Specialized teams can help the doctor with this task. For instance, a provider with a diabetes patient can search for a diabetes specialist team and assign the patient to the team or to a subset thereof (such as a single doctor). The aggregator 120 may also provide functionality for the provider to create a subteam from an existing team. Such functionality may be useful, for instance, to create a team of specialist doctors that are currently at a hospital as a subset of all diabetes doctors in a given team (some of whom may be off duty). Further, such functionality may also be useful because there may be many teams in a hospital or other healthcare setting and it may be difficult to locate the right team in a large healthcare institution without such functionality.

In one embodiment, the teams described above are organized into services that correspond to functional groups of providers, which may be defined along the lines of medical and surgical specialties. For example, multiple teams can be created for Internal Medicine, General Surgery, or Gynecology services, among others. Services provide a way to organize teams, making relevant teams easier to find in the system. Additionally, teams of the same service may share the same user interface, which can be based on a template specific to the service. For example, surgeons may want to see the date of prior operation and drain output data on their patient grid, but internal medicine physicians may want to track the patient's smoking status and other cardiovascular risk factors. Using service-specific templates, in certain embodiments the teams on a particular service can receive similar user interfaces that are tailored to the goals of the particular service.

Further, in certain embodiments some or all messages are tagged with the name of the service (or other identifier thereof) which originated them. This tagging can allow convenient filtering of messages that are relevant to the service.

Tagging can provide additional benefits when multiple teams on different services take care of the same patient. This is a frequent occurrence. For example, when a trauma patient (primarily assigned to a general surgery team) is followed by Neurology, Orthopedics or Gastroenterology consulting teams. These teams may share some of the same patient data (such as name, age, history of present illness, allergies, etc.), but may choose to keep separate tasks, comments, and issues (and/or other types of messages). This filtered message flow can be easily accomplished when the user chooses to view only the messages generated by the user's service.

FIGS. 15 through 18 depict example user interfaces 1500-1800 that can be relevant to services. Any of these user interfaces 1500-1800 may be used in conjunction with or replacement for certain of the user interfaces described above. For instance, FIG. 15 illustrates an example service selector user interface 1500 that enables users to filter teams by services. The user interface 1500 includes a filter by service control 1510 that can provide a drop-down box of services. Before selection of this filter, multiple teams 1520 and 1530 are shown from different services (including "My Teams" 1520 in Family Medicine and "Other Teams" 1530 in multiple services). Selecting a service in the filter by service control 1510 and pressing a "go" button 1512 can can result in the example user interface 1600 of FIG. 16 being output for display. As shown, the depicted teams 1520, 1530 include teams that are associated with the selected Family Medicine service. A team's service affiliation can be edited by selecting the "Edit" link 1522 next to each team in either user interface 1500, 1600, and services in general can be edited by selecting the "Edit Services" link 1532 in either user interface 1500, 1600.

FIG. 17 depicts an example service grid user interface 1700. Like the patient grids described above (see, e.g., FIG. 8), the service grid user interface 1700 includes a grid 1700 that depicts characteristics of one or more patients. The example grid 1700 shown is associated with a particular service, the Radiology IR service, and a team within that service, the "IR Consult" team. The layout of the grid is base on the template specific to the Radiology IR service. The grid contains the column "Service Info" which displays information specific to the Radiology IR service (and which may be hidden from other services that may be caring for the same patient). Although some templates can hide certain information for convenience, in some embodiments all information available to the different services can be accessed (e.g., by an appropriate user, such as a physician) from the patient information user interface or detailed view in the interest of full transparency (see, e.g., FIGS. 6A, 6B)

Figure 18:
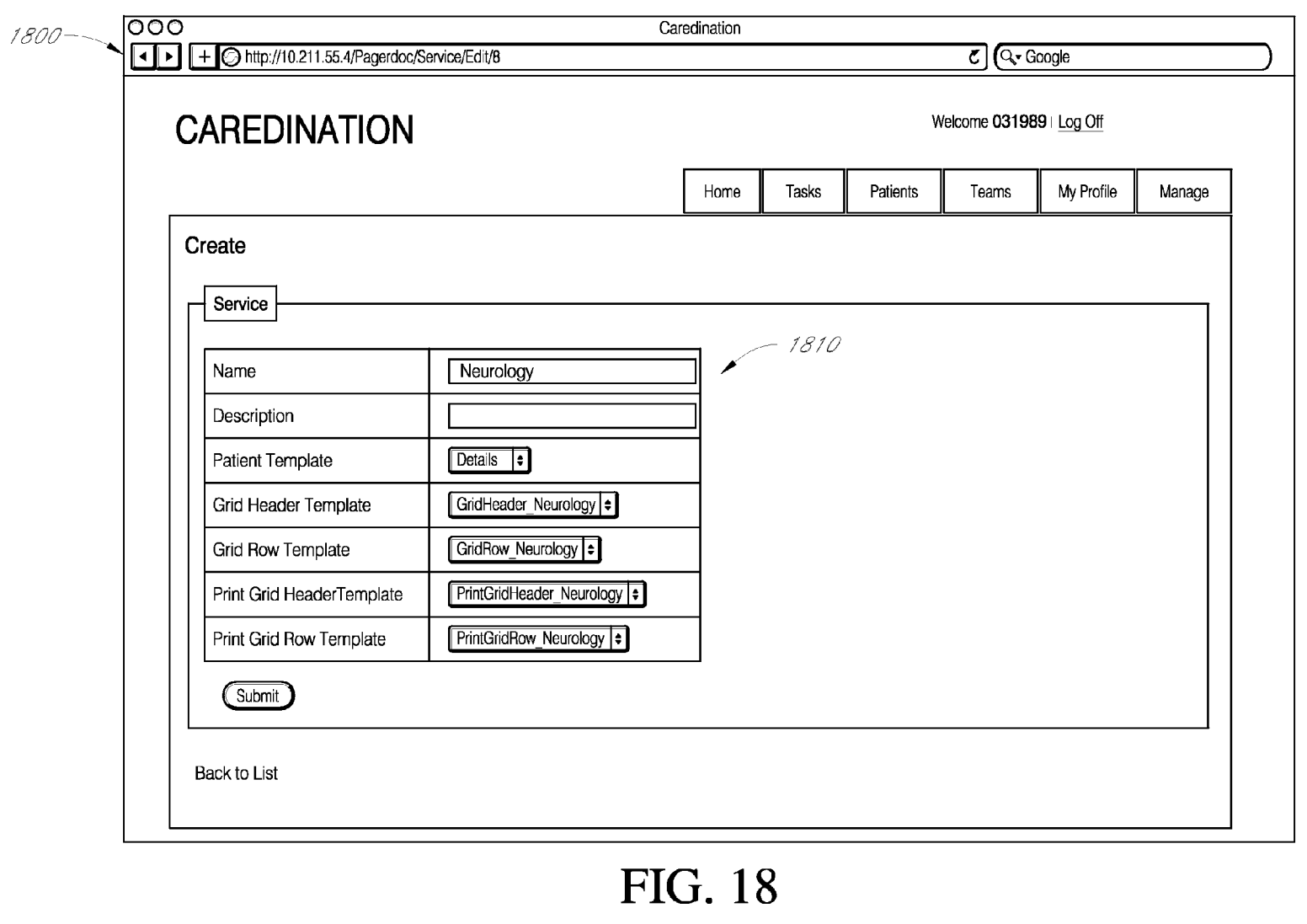

FIG. 18 depicts an example service creation user interface 1800 that enables a service to be created. User interface controls 1810 are provided for defining the name of the service, a description of the service, and various templates that can be associated with the service as described above. These templates may be edited in a separate user interface (not shown).

V. Patient Status and Team Base Embodiments

In certain embodiments, each patient has a status that identifies whether the patient is an inpatient or an outpatient. When the patient is admitted to the hospital the status can be set to inpatient, and when the patient is sent home, the status can change to outpatient. Likewise, teams may be based in the inpatient and outpatient setting. Consequently, teams can have a base setting of inpatient or outpatient. The aggregator 120 can tailor the display of patients with regard to their status and the team base. For instance, the aggregator 120 can match the patient status and team base to generate the primary patient list for the team. Thus, for example, an inpatient team can receive a list or grid of inpatients, and an outpatient team can receive a list or grid of outpatients. Further, any of the teams, including both inpatient and outpatient teams, may also include non-clinician service providers who can benefit from access to patient information, such as social workers.

When an inpatient gets discharged (and his/her status changes to outpatient), the patient can remain associated with the inpatient team while falling off the primary patient list. However, the patient can continue to be displayed in one or more secondary lists available to clinicians in the hospital. Continuing to provide access to these outpatients to clinicians in the hospital can be useful because clinicians in the hospital may need to follow up on lab tests or appointments for the patients they have previously discharged. Lack of such follow-up can lead to unnecessary hospital readmissions, a preventable and significant source of waste in healthcare.

In one embodiment of the current system, a hospital clinician can look at a secondary list of discharged inpatients to identify patients that need outpatient follow-up. The clinician can use the system's messaging functionality to set himself/herself a task and be prompted to complete the task when the time for follow-up comes. The task can prompt the physician because the logical connection between the patient and clinician may persist through the inpatient-to-outpatient transition. The aggregator 120 can use customizable business logic to generate secondary lists of patients. In one embodiment of the secondary list, the aggregator 120 displays a watch list of discharged patients (outpatients attached to an inpatient team) who have a pending incomplete task (such as following up on lab results). The aggregator 120 can also continue to provide clinicians with access to messages and the other features described herein for outpatients. In an embodiment, task alerts and messages are filtered based on team base, such that an inpatient team is notified of tasks and messages for an inpatient instead of an outpatient team (such as a clinic physician) associated with the inpatient. However, the outpatient team may still have access to the task alerts and messages and may choose to continue to receive such alerts and messages in some instances.

Likewise, when an outpatient is attached to an outpatient team, the patient can appear on the outpatient team's primary list. The outpatient team can access the team's primary list through the features of the aggregator 120, even when the clinicans in the output team are outside of the hospital. For instance, physicians at clinics can access the features of the aggregator 120 to monitor their patients who become inpatients and continue to monitor those patients when they are discharged. Allowing clinicians outside of the hospital to continue to monitor their patients during and after a hospital stay may be useful for clinic physicians to keep track of their patients. In an embodiment, a patient is admitted to a hospital, the patient would fall off the primary list of the outpatient clinician. The aggregator 120 can display such a patient in a secondary list of the outpatient clinician, which list could be a list of inpatients attached to an outpatient team. Using such a list, the clinic physician can follow the patient's hospital course and participate in the patient's care throughout the continuum of care. Thus, in certain embodiments, the aggregator 120 can advantageously prevent situations where a clinic physician is unaware of one of his or her patients being admitted to the hospital. The aggregator 120 can be implemented in the cloud, or more generally, in one or more servers or other computing devices accessible by clinicians both inside and outside of the hospital to facilitate this continuum of care functionality.

Figure 19:
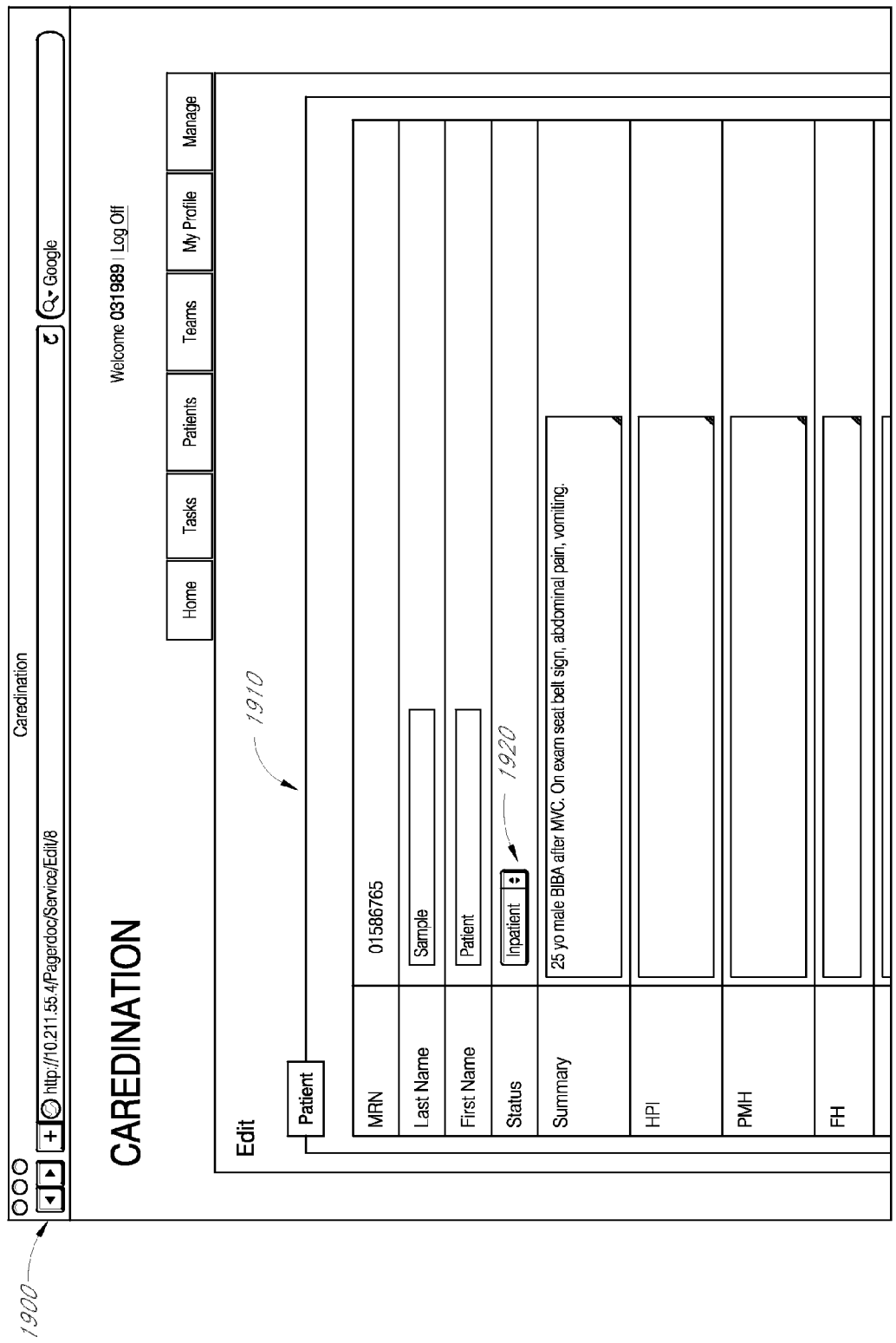
Figure 20:
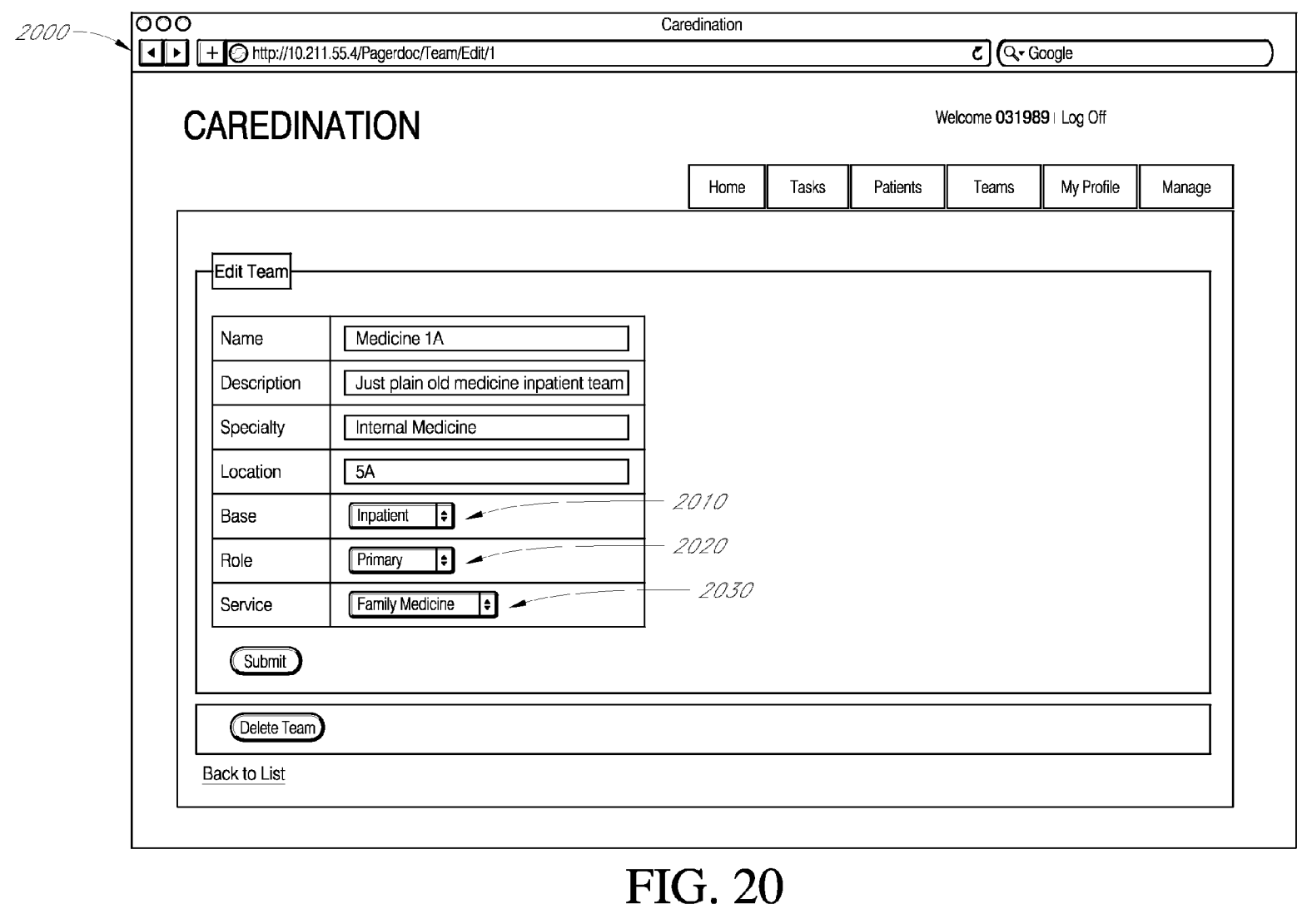
Figure 21:
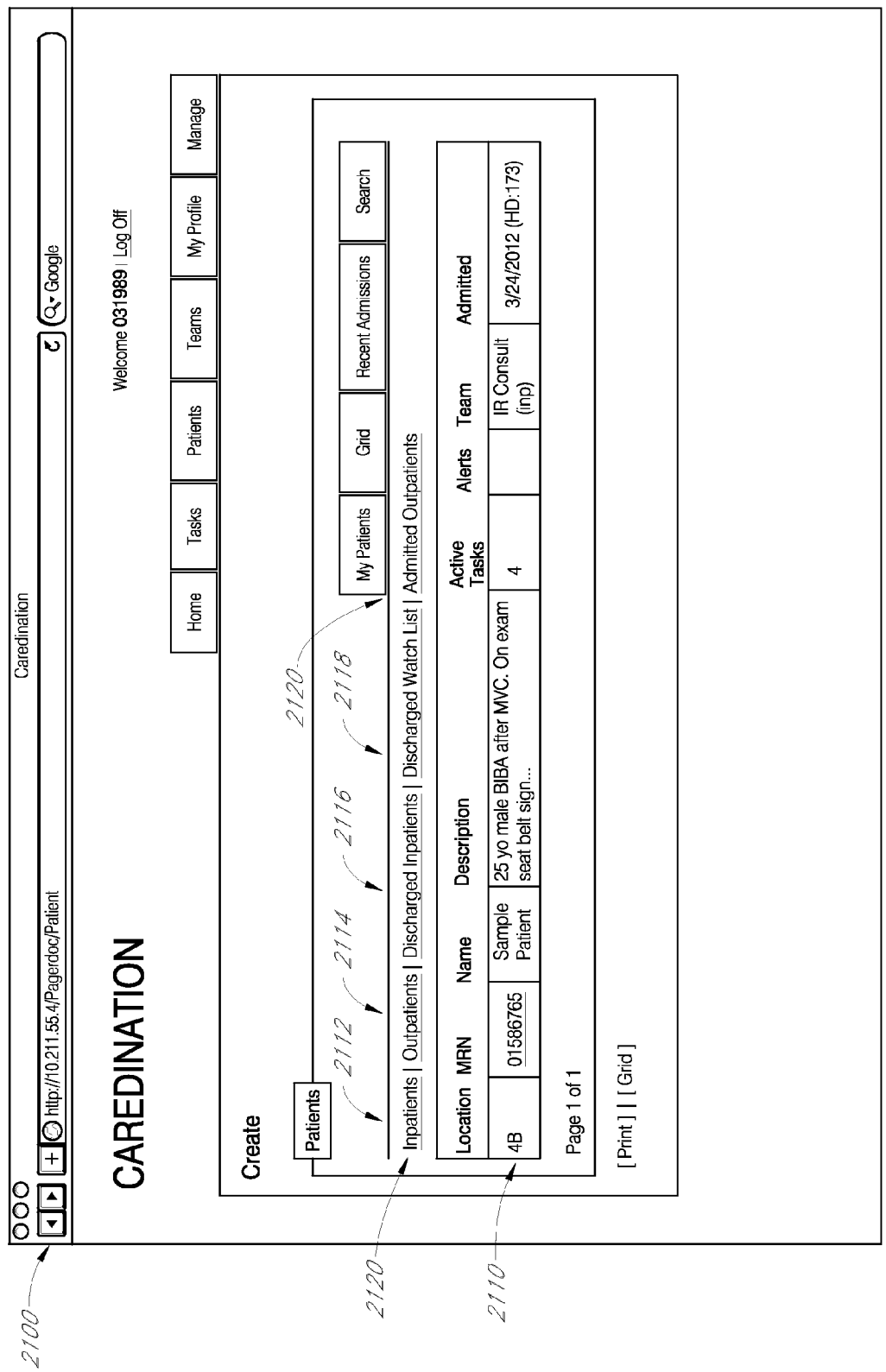

FIGS. 19 through 21 depict example user interfaces 1900-2100 that can be relevant to patient status. For example, FIG. 19 depicts an example patient status user interface 1900 that includes controls 1910 for editing patient data. One of these controls 1910, a status control 1920, is a selector for the status of the patient. A user can select "Inpatient" or "Outpatient" status 1920 to change the patient's status from inpatient to outpatient or vice versa.

FIG. 20 depicts an example team edit user interface 2000 that includes features for defining teams with respect to patient status. A user can define the base of the team by choosing either the inpatient or outpatient base using control 2010. The use can also assign a role to the team using control 2020 by selecting either a primary or consult role. If the primary role is selected, the patients on the team can appear on the primary list for the team, whereas the patients can appear on a secondary list for the team if the consult role is selected. A user can also assign a service to the team using control 2030 by selecting from the previously defined services.

FIG. 21 depicts an example patient list user interface 2100. This user interface 2100 demonstrates an example menu of secondary lists of patients 2110 (with a single example patient shown). A menu 2120 includes various options to view different patients, including an inpatients option 2112 (the primary list of inpatients attached to an inpatient team, which may be displayed by default), an outpatients option 2114 (e.g., outpatients attached to an outpatient team), a discharged inpatients option 2116 (e.g., outpatients attached to the inpatient team), a discharged watch list option 2118 (e.g., outpatients attached to the inpatient team who still have an active task), and an admitted outpatients option 2120 (e.g., inpatients attached to an outpatient team). The user interface 2100 can advantageously allow teams to filter for certain types of patients (e.g., inpatients or outpatients), thereby avoiding cluttering the user interface with all patients (although all patients of a team may be viewed in one embodiment if desired).

VI. Checklists and Tasks Embodiments

Certain events in the continuum of care (such as admissions, discharges, and transfers) involve certain standard sequences of clinician actions (such as for surgery, diagnoses, tests, etc.). As multiple patients go through such events, tend to clinician generate the same sequences of tasks for multiple patients. This process can be laborious and repetitive and also may be prone to human error, since an individual clinician may forget to create an important standard task. One implementation of the aggregator 120 can provide checklists associated with aforementioned events. These checklists can contain items that can be converted to tasks at will, thereby automating the process of task generation. The checklists can be useful because they can remind clinicians of a standard sequence of tasks, thereby reducing the possibility of human. The automated creation of tasks using checklists can also save clinicians time. For example, each checklist can include a list or template of tasks that the aggregator 120 can cause to auto-generate tasks when the checklist is selected for a particular patient by a clinician. The aggregator 120 can provide a management user interface to generate checklists, which may be specific to a service or services, or specific to a team or teams. Users can obtain a selection of checklists from the patient user interfaces or other user interfaces described above (e.g., such as FIGS. 6A through 8) and apply multiple tasks to a patient at one time.

In one implementation of the system, there is a user interface, which lists the patients in a tile format with a simplified view of tasks displayed. This interface provides an uncluttered view of pending tasks, allowing providers to quickly plan their workflow and to monitor task completion. FIG. 22 depicts an example of such a patient list user interface 2100 that demonstrates an alternative display of patients 2210 in a tiled view with a brief description and the list of active tasks 2220 for each patient.

VII. Additional Example Embodiments

The aggregator 120, including messages, information user interfaces and grids, as well as team management functions, can be accessed with standard web browsers on the healthcare facility's local area network. Users may access the aggregator 120 from the computers directly connected to the LAN or from the mobile devices that securely connect to the facility wireless network (Wi-Fi). Alternatively, the aggregator 120 may publish an Application Programming Interface (API), which would allow appropriately credentialed and provisioned devices and application to access the aggregator 120's information. A possible embodiment of such client application is a native program on a mobile device, which accesses the aggregator 120 through a defined web service address, presenting appropriate security credentials. The client application can use appropriate protocols (such as SOAP or REST) to exchange information with the aggregator 120, allowing users immediate real-time (or rapid) access to the flow of messages. Further, the routing capability of the aggregator 120 can be used to initiate IP-based voice communication. For example, a provider may send a specialized message (dynamically routed in the standard fashion) to a mobile device. The provider with the device immediately initiates a VoIP connection with the sender of the message. Moreover, messages can have the capability to optionally attach other documents, such as photographs, radiological images, textual and/or multimedia documents to the body of the message. Other forms of communications, such as links to other online media or voice/video recordings could likewise be embedded.

So far a system of messaging within a local area network has been discussed. Such a system communicates with the outside Wide Area Network (WAN) through the institution's firewall, in order to access the common facilities for paging and messaging. A possible embodiment of the aggregator 120 may have secure connections across the WAN with facilities for common servicing and maintenance of the aggregator 120. Connections could also exist among such systems at different healthcare institutions, allowing free secure communication among providers in multiple settings, including outpatient settings, doctor's office settings, nursing homes, and home care settings, among others. Moreover, some or all the functions of the aggregator 120, such as data storage and messaging, could be centralized in a scalable "cloud" infrastructure, leveraging efficiencies of scale and minimizing cost for healthcare providers and institutions. Extending this concept further, a super aggregator could be established in a cloud computing platform or in one or more data centers, which would enable collaboration of patient information, handoffs, and messaging among multiple clinical facilities, including hospitals, doctors' offices, pharmacies, labs, in-home healthcare, and the like.

Further, although this specification describes handoff, messaging, compliance, and other features in the context of teams, it should be understood that teams are not necessary in every implementation. Instead, in some embodiments, individual providers can access the handoff, messaging, and/or compliance functions of the aggregator 120. Moreover, any of the user interfaces described herein may include different user interface controls for the same functionality shown herein.

Data gathered by the aggregator 120 can be leveraged to create reports on a variety of different metrics. For instance, the aggregator 120 can include a reporting component (not shown) that can use the data regarding provider sign-ins and sign-outs combined with patient discharge data to evaluate discharge rates, determine individual providers' discharge rates, and so on.

In some embodiments, a goal of the day or the like for a patient (such as a progress goal for the patient) can be posted in the messaging user interface. The aggregator 120 can also provide prompts or reminders to review or write content, such as certain messages or reports.

The aggregator 120 can provide increased patient privacy by reducing patient information exposure on white boards. Even in hospitals where patient names are replaced by room numbers on white boards, privacy is still at risk. The aggregator 120 can completely eliminate the usage of white boards for tracking patient data, provider scheduling, and so forth.

In some embodiments, the aggregator 120 can include a translation component or access a translation service via a web service or remote procedure call. The translation component or service can provide functionality for translation messages into different languages for different providers or patients, enabling providers of different cultures to communicate more effectively. The aggregator 120 could also include other assistance tools, such as tools for reading words of messages out loud for blind persons or the like.

The aggregator 120 can provide different levels of access or functionality to different persons. Some persons may be granted full access to messages and patient data, while others are presented with more limited views, for example, based on HIPAA or other privacy laws. Supervisors may have additional functions from the aggregator 120 than trainees or subordinates, for example. Managers may also have different functions from providers as described above.

The messages provided by the messaging user interface 700 can be generated using templates in one embodiment. These templates can include common phrases, words, sentences, images, or video that can be used to more rapidly create messages. Further, images of patients, video, or lab results (images or video) can also be included in some embodiments.

The aggregator 120 may also be able to communicate over a network with an application, such as a mobile application or web service-based application. The application can provide any of a variety of features. For instance, the application may be a secure application that enables families of patients to do any subset of the following: check messages made regarding those patients, determine which doctor(s) is seeing a patient at any given time (so as to be able to direct questions to the correct doctor), ask questions and communicate with doctors and patients via the messaging user interface, email concerns or questions (such as "what time is the surgery tomorrow"?), and the like. Family members' contact info can be posted in the messaging user interface or another user interface, enabling doctors to contact family members. Living wills, powers of attorney, and other legal documents can also be attached to patient records in the user interfaces provided by the aggregator 120. Features can be provided for patients to upload such documents to the aggregator 120.

In existing environments, patient charts are often left at beds mistakenly. Thus, patient privacy is breached when subsequent patients come to the facility. Further, due to this common error, patient charts can be mixed together, causing potential life-jeopardizing problems. In contrast, the aggregator 120 can reduce or eliminate these problems altogether by keeping electronic charts of patients via the patient information and messaging user interfaces, among other features. Generally speaking, the patient charts and other features of the aggregator 120 can provide a patient-centered initiative, such that the aggregator 120 in some embodiments is not just a system for sharing information, but also a system for enabling providers to have a patient care-focused conversation or dialogue that can improve coordination of care.

In several embodiments, the aggregator 120 functions as an add-on component of the EHR (Electronic Health Record) system or EMR system, supplementing current functionality with enhanced messaging and dynamic routing capabilities. Although this implementation is made seamless in some embodiments with the EHR from the workflow standpoint by the use of single sign-on technologies and integration interfaces, the aggregator 120 can still be a stand-alone system. In another embodiment, the aggregator 120 can perform the totality of the functions of the EHR, thereby wrapping the medical data in the messaging functionality, and user-defined dynamic actions. In this embodiment, the concepts of dynamic determination of the provider in charge of the patient, dynamic conditional routing of messages and the resulting electronic dialogue can be used as guiding principle in constructing the EHR's of the future. Wrapping medical data (including, for example, medications, problems, etc) into messaging functionality with dynamic logic (e.g., actions) can therefore be an advantageous paradigmatic shift from the current static representation of data in the Electronic Health or Medical Records (EHR/EMR).

VIII. Terminology

Many other variations than those described herein can be apparent from this disclosure. For example, depending on the embodiment, certain acts, events, or functions of any of the algorithms described herein can be performed in a different sequence, can be added, merged, or left out all together (e.g., not all described acts or events are necessary for the practice of the algorithms). Moreover, in several embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together. Although certain computer-implemented tasks are described as being performed by a particular entity, other embodiments are possible in which these tasks are performed by a different entity.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that several embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, several embodiments of the inventions described herein can be embodied within a form that does not provide all of the features and benefits set forth herein, as some features can be used or practiced separately from others.

What is claimed is:

1. A method of making patient care messages available to healthcare providers on different shifts, the method comprising:

electronically generating a provider assignment user interface for presentation to a user, the provider assignment user interface comprising functionality for the user to assign a patient to a first team of healthcare providers;

in response to the patient being assigned to the first team of healthcare providers:

providing the first team of healthcare providers with access to a patient messaging user interface implemented by a messaging component, wherein the patient messaging user interface enables the first team of healthcare providers to electronically post messages regarding care of the patient for access by each member of the first team of healthcare providers and for access by a second team of healthcare providers subsequently assigned to the patient, without requiring the members of the first team of healthcare providers to know an identity of any of the second team of healthcare providers when electronically posting the messages, wherein the messages comprise a task having a deadline;

providing a patient handoff user interface implemented by a handoff component, the patient handoff user interface providing functionality for care of the patient to be handed off from the first team of healthcare providers to the second team of healthcare providers; and providing, with the messaging component, the second team of healthcare providers with access to the posted messages regarding the patient posted by the first team of healthcare providers in response to a handoff of the patient care occurring via the patient handoff user interface, wherein said providing the second team with access to the posted messages comprises sending a notification of a first message regarding the task to a member of the second team of healthcare providers that is a student provider before sending the notification to a supervisory provider of the second team of healthcare providers;

in response to the messaging component determining that the student provider failed to respond to the first message, escalating the notification of the task to the supervisory provider; and in response to the messaging component determining that neither the student provider nor the supervisory provider viewed the first message within a selected time frame, notifying, with the messaging component, an originator of the first message that the first message has not been viewed within the selected time frame;

wherein the messaging component and the handoff component are implemented by a computer system comprising computer hardware.

2. The method of claim 1, wherein the patient messaging user interface is further configured to provide micro-blogging tools to create the messages.

3. The method of claim 2, wherein the micro-blogging tools provide functionality to post one or both of a comment and a question in reply to each of the posted messages.

4. The method of claim 1, wherein the patient messaging user interface is further configured to use a social networking format for generation of the messages.

5. The method of claim 1, wherein the patient messaging user interface further comprises functionality for creating tasks.

6. The method of claim 5, wherein the patient messaging user interface further comprises functionality for performing one or more of the following: assigning deadlines to the tasks and setting notification parameters for the tasks.

7. The method of claim 6, further comprising notifying the second team of healthcare providers of a task created by a member of the first team of healthcare providers.

8. A system for making patient care messages available to healthcare providers on different shifts, the system comprising:
- a patient handoff component configured to provide a patient handoff user interface that provides functionality for care of a patient to be handed off from a first team of healthcare providers initially assigned to care for the patient to a second team of healthcare providers subsequently assigned to care for the patient; and
- a messaging component comprising computer hardware, the messaging component configured to:
  - provide the first team of healthcare providers with access to a patient messaging user interface while the first team of healthcare providers is assigned to care for the patient, the patient messaging user interface configured to enable members of the first team of healthcare providers to post messages regarding care of the patient for access by each other and by the second team of healthcare providers, without the first healthcare provider having to know an identity of the second healthcare provider;
  - in response to care of the patient being transferred from the first team of healthcare providers to the second team of healthcare providers, automatically provide the second team of healthcare providers with access to the posted messages regarding the patient posted by the first team of healthcare providers,
  - send a notification of a first message to a member of the second team of healthcare providers that is a student provider before sending the notification to a supervisory provider of the second team of healthcare providers;
  - determine that the student provider failed to respond to the first message, and in response, contact the supervisory provider regarding the first message; and
  - determine that neither the student provider nor the supervisory provider viewed the first message within a selected time frame, and in response, notify a sender of the first message that the first message has not been viewed within the selected time frame.

9. The system of claim 8, wherein the patient messaging user interface further comprises functionality for creation of a task by the first team of healthcare providers.

10. The system of claim 9, wherein the messaging component is configured to notify the second team of healthcare providers of a deadline for completing the task.

11. The system of claim 8, further comprising a compliance component configured to track hours worked of one or more members of the first and second team of healthcare providers so as to enable reporting of their hours worked to a regulatory agency.

12. The system of claim 11, wherein the compliance component is further configured to automatically report the hours worked to the regulatory agency as evidence of compliance with regulations regarding medical trainee working hours.

13. The system of claim 8, wherein the patient handoff user interface is further configured to enable handoff of care of the patient in one or more of the following situations: from a first healthcare facility to a second healthcare facility, from the first healthcare facility to a home healthcare scenario, and from a home healthcare scenario to the first healthcare facility.

14. The system of claim 8, wherein the messaging component is further configured to first notify a first member of the second team of healthcare providers who is designated to receive notifications before notifying other members of the second team of healthcare providers.

15. The system of claim 14, wherein the messaging component is further configured to notify a second member of the second team of healthcare providers subsequent to notifying the first member in response to determining that the first member failed to respond to the notification.

16. The system of claim 15, wherein said notifying the second member allows the second member to monitor medical training of the first member.

17. The system of claim 16, wherein the first member is selected from the group consisting of an intern and a resident and wherein the second member is selected from the group consisting of a resident, a fellow, and an attending physician.

18. The system of claim 8, further comprising a service selector user interface that provides functionality for filtering the first and second teams based on services associated with those teams.

19. The system of claim 8, further comprising a patient list user interface that provides functionality for filtering patients based on an inpatient or outpatient status of the patients.

20. The system of claim 8, wherein the system is further configured to enable a third team of outpatient healthcare providers to be associated with inpatients to thereby enable the outpatient healthcare providers to continue monitoring their patients when their patients are admitted to a hospital.

21. The system of claim 8, wherein the system is further configured to output a checklist that auto-creates a plurality of tasks related to healthcare of the patient in response to user selection of the checklist.

22. Non-transitory physical computer storage comprising instructions stored thereon that, when executed by one or more processors, cause the one or more processors to implement a system for making patient care messages available to healthcare providers on different shifts, the system comprising:
- a messaging component configured to:
  - electronically generate a patient messaging user interface;
  - provide a first team of healthcare providers with access to the patient messaging user interface while the first team of healthcare providers is assigned to care for the patient,
  - the patient messaging user interface configured to enable the first team of healthcare providers to post messages regarding care of the patient for access by each member of the first team of healthcare providers and by a second team of healthcare providers, without the first team of healthcare providers having to know an identity of the second team of healthcare providers when posting the messages;
  - automatically provide the second team of healthcare providers with access to the posted messages regarding the patient posted by the first team of healthcare providers in response to care of the patient being transferred from the first team of healthcare providers to the second team of healthcare providers;

send a notification to a first provider of the second team of healthcare providers before sending the notification to a second provider of the second team of healthcare providers;

determine that the first provider failed to access the notification, and in response, escalate the notification to the second provider; and determine that neither the first provider nor the second provider accessed the notification, and in response, notify a third provider that the notification has not been accessed.

23. The non-transitory physical computer storage of claim 22, wherein the messaging component is further configured to automatically provide the second team of healthcare providers with access to the posted messages in real-time.

24. The non-transitory physical computer storage of claim 22, wherein the patient messaging user interface comprises user interface controls configured to enable the first team of healthcare providers to post said messages.

25. The non-transitory physical computer storage of claim 22, in combination with a computer system comprising computer hardware.

* * * * *